US009994768B2

(12) United States Patent
Furusato et al.

(10) Patent No.: US 9,994,768 B2
(45) Date of Patent: Jun. 12, 2018

(54) LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Yoshimasa Furusato, Chiba (JP); Masayuki Saito, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days. days.

(21) Appl. No.: 15/035,486

(22) PCT Filed: Oct. 3, 2014

(86) PCT No.: PCT/JP2014/076527
§ 371 (c)(1),
(2) Date: May 10, 2016

(87) PCT Pub. No.: WO2015/072243
PCT Pub. Date: May 21, 2015

(65) Prior Publication Data
US 2016/0280995 A1 Sep. 29, 2016

(30) Foreign Application Priority Data

Nov. 13, 2013 (JP) .................................. 2013-235285

(51) Int. Cl.
| | | |
|---|---|---|
| G02F 1/1333 | (2006.01) |
| C09K 19/34 | (2006.01) |
| C09K 19/30 | (2006.01) |
| C07C 25/18 | (2006.01) |
| C07C 43/205 | (2006.01) |
| C07C 43/215 | (2006.01) |
| C07D 309/06 | (2006.01) |
| C09K 19/54 | (2006.01) |
| G02F 1/1362 | (2006.01) |
| C09K 19/04 | (2006.01) |
| C09K 19/12 | (2006.01) |

(52) U.S. Cl.
CPC .......... *C09K 19/3402* (2013.01); *C07C 25/18* (2013.01); *C07C 43/205* (2013.01); *C07C 43/215* (2013.01); *C07D 309/06* (2013.01); *C09K 19/3001* (2013.01); *C09K 19/3003* (2013.01); *C09K 19/3066* (2013.01); *C09K 19/3068* (2013.01); *C09K 19/542* (2013.01); *G02F 1/1362* (2013.01); *C07C 2601/14* (2017.05); *C09K 2019/0444* (2013.01); *C09K 2019/0448* (2013.01); *C09K 2019/122* (2013.01); *C09K 2019/123* (2013.01); *C09K 2019/301* (2013.01); *C09K 2019/3004* (2013.01); *C09K 2019/3009* (2013.01); *C09K 2019/3016* (2013.01); *C09K 2019/3422* (2013.01); *C09K 2019/3425* (2013.01); *C09K 2019/548* (2013.01)

(58) Field of Classification Search
CPC ............ C09K 19/3402; C09K 19/3003; C09K 19/3068; C09K 19/3001; C09K 19/3066; C09K 19/542; C09K 2019/0444; C09K 2019/0448; C09K 2019/3016; C09K 2019/3425; C09K 2019/3004; C09K 2019/3009; C09K 2019/301; C09K 2019/3422; C09K 2019/548; C09K 2019/122; C09K 2019/123; C07C 25/18; C07C 43/205; C07C 43/215; C07C 2601/14; G02F 1/1333; G02F 1/1362; C07D 309/06
USPC ......................... 252/299.01, 299.61; 428/1.1
See application file for complete search history.

(56) References Cited

U.S. PATENT DOCUMENTS

| | | | |
|---|---|---|---|
| 8,821,993 B2 * | 9/2014 | Hattori ............... | C09K 19/3066 252/299.61 |
| 2013/0207039 A1 | 8/2013 | Hattori et al. | |
| 2015/0069296 A1 | 3/2015 | Kuriyama et al. | |
| 2015/0232757 A1 | 8/2015 | Kaneoya et al. | |
| 2016/0009995 A1 | 1/2016 | Kuriyama et al. | |

FOREIGN PATENT DOCUMENTS

| | | |
|---|---|---|
| CN | 101142160 | 3/2008 |
| EP | 0969071 | 1/2000 |
| JP | 2005281559 | 10/2005 |
| JP | 2006306756 | 11/2006 |

(Continued)

OTHER PUBLICATIONS

"International Search Report (Form PCT/ISA/210) of PCT/JP2014/076527", with English translation thereof, dated Jan. 13, 2015, pp. 1-4.
"Office Action of China Counterpart Application," with English translation thereof, dated Jul. 13, 2016, p. 1-p. 21, in which the listed reference was/references were cited.

*Primary Examiner* — Geraldina Visconti
(74) *Attorney, Agent, or Firm* — JCIPRNET

(57) ABSTRACT

The composition contains a specific compound having a high maximum temperature and a low minimum temperature as a first component and has negative dielectric anisotropy, and may further contain a specific compound having large negative dielectric anisotropy as a second component, a specific compound having a high maximum temperature or small viscosity as a third component, a specific compound having large negative dielectric anisotropy as a fourth component and a specific compound having a polymerizable group as an additive component.

14 Claims, No Drawings

(56) References Cited

FOREIGN PATENT DOCUMENTS

| | | |
|---|---|---|
| JP | 2008-058374 | 3/2008 |
| JP | 2008-308581 | 12/2008 |
| JP | 2014-196474 | 10/2014 |
| JP | 2014-208842 | 11/2014 |
| TW | 201337347 | 9/2013 |
| WO | 2012053323 | 4/2012 |
| WO | 2014041985 | 3/2014 |
| WO | 2013094596 | 4/2015 |

* cited by examiner

LIQUID CRYSTAL COMPOSITION AND LIQUID CRYSTAL DISPLAY DEVICE

CROSS-REFERENCE TO RELATED APPLICATION

This application is a 371 application of the international PCT application serial no. PCT/JP2014/076527, filed on Oct. 3, 2014, which claims the priority benefit of Japan application no. 2013-235285, filed on Nov. 13, 2013. The entirety of each of the above-mentioned patent applications is hereby incorporated by reference herein and made a part of this specification.

TECHNICAL FIELD

The invention relates to a liquid crystal composition, a liquid crystal display device including the composition, and so forth. In particular, the invention relates to a liquid crystal composition having a negative dielectric anisotropy, and a liquid crystal display device including the liquid crystal composition and having a mode such as an IPS mode, a VA mode, an FFS mode and an FPA mode. The invention also relates to a liquid crystal display device having a polymer sustained alignment mode.

BACKGROUND ART

In a liquid crystal display device, a classification based on an operating mode for liquid crystal molecules includes a phase change (PC) mode, a twisted nematic (TN) mode, a super twisted nematic (STN) mode, an electrically controlled birefringence (ECB) mode, an optically compensated bend (OCB) mode, an in-plane switching (IPS) mode, a vertical alignment (VA) mode, a fringe field switching (FFS) mode and a field induced photo-reactive alignment (FPA) mode. A classification based on a driving mode in the device includes a passive matrix (PM) and an active matrix (AM). The PM is classified into static and multiplex and so forth. The AM is classified into a thin film transistor (TFT), a metal insulator metal (MIM) and so forth. The TFT is further classified into amorphous silicon and polycrystal silicon. The latter is classified into a high temperature type and a low temperature type based on a production process. A classification based on a light source includes a reflection type utilizing natural light, a transmissive type utilizing backlight and a transflective type utilizing both the natural light and the backlight.

A liquid crystal display device includes a liquid crystal composition having a nematic phase. The composition has suitable characteristics. An AM device having good characteristics can be obtained by improving the characteristics of the composition. Table 1 below summarizes a relationship in two characteristics. The characteristics of the composition will be further described based on a commercially available AM device. A temperature range of the nematic phase relates to a temperature range in which the device can be used. Preferred maximum temperature of the nematic phase is about 70° C. or higher, and a preferred minimum temperature of the nematic phase is about −10° C. or lower. Viscosity of the liquid crystal composition relates to a response time in the device. A short response time is preferred for displaying moving images on the device. A shorter response time even by one millisecond is desirable. Accordingly, a small viscosity of the composition is preferred. A small viscosity at a low temperature is further preferred.

TABLE 1

Characteristics of Composition and AM Device

| No. | Characteristics of Composition | Characteristics of AM Device |
|---|---|---|
| 1 | Wide temperature range of a nematic phase | Wide usable temperature range |
| 2 | Small viscosity[1] | Short response time |
| 3 | Suitable optical anisotropy | Large contrast ratio |
| 4 | Large positive or negative dielectric anisotropy | Low threshold voltage and small electric power consumption Large contrast ratio |
| 5 | Large specific resistance | Large voltage holding ratio and large contrast ratio |
| 6 | High stability to ultraviolet light and heat | Long service life |

[1] A liquid crystal composition can be injected into a liquid crystal display device in a short time.

An optical anisotropy of the composition relates to a contrast ratio in the device. According to a mode of the device, a large optical anisotropy or a small optical anisotropy, more specifically, a suitable optical anisotropy is required. A product ($\Delta n \times d$) of the optical anisotropy ($\Delta n$) of the composition and a cell gap (d) of the device is designed so as to maximize the contrast ratio. A suitable value of the product depends on a type of the operating mode. The suitable value is in the range of about 0.30 to 0.40 micrometer in a device having the VA mode, and is in the range of about 0.20 to 0.30 micrometer in a device having the IPS mode or the FFS mode. In the above cases, a composition having the large optical anisotropy is preferred for a device having a small cell gap. The large dielectric anisotropy in the composition contributes to a low threshold voltage, a small electric power consumption and a large contrast ratio in the device. Accordingly, the large dielectric anisotropy is preferred. A large specific resistance in the composition contributes to a large voltage holding ratio and the large contrast ratio in the device. Accordingly, a composition having a large specific resistance at room temperature and also at a temperature close to the maximum temperature of the nematic phase in an initial stage is preferred. A composition having a large specific resistance at room temperature and also at a high temperature after the device has been used for a long period of time is preferred. Stability of the composition to ultraviolet light and heat relates to a service life of the liquid crystal display device. In the case where the stability is high, the device has a long service life. Such characteristics are preferred for an AM device used in a liquid crystal projector, a liquid crystal television and so forth.

In a liquid crystal display device having a polymer sustained alignment (PSA) mode, a liquid crystal composition containing a polymer is used. First, a composition to which a small amount of a polymerizable compound is added is injected into the device. Then, the composition is irradiated with ultraviolet light while voltage is applied between substrates of the device. The polymerizable compound polymerizes to form a network structure of the polymer in the liquid crystal composition. In the composition, alignment of liquid crystal molecules can be controlled by the polymer, and therefore a response time in the device is shortened and also image persistence is improved. Such an effect of the polymer can be expected for a device having the mode such as the TN mode, the ECB mode, the OCB mode, the IPS mode, the VA mode, the FFS mode and the FPA mode.

A composition having a positive dielectric anisotropy is used for an AM device having the TN mode. In an AM device having the VA mode, a composition having a negative dielectric anisotropy is used. A composition having a positive or negative dielectric anisotropy is used for an AM device having the IPS mode or the FFS mode. In an AM device having a polymer sustained alignment (PSA), a composition having a positive or negative dielectric anisotropy is used. An example of the liquid crystal composition having the negative dielectric anisotropy is disclosed in following Patent literature No. 1.

CITATION LIST

Patent Literature

Patent literature No. 1: WO 2012-053323 A

SUMMARY OF INVENTION

Technical Problem

One of aims of the invention is to provide a liquid crystal composition satisfies at least one of characteristics such as a high maximum temperature of a nematic phase, a low minimum temperature of the nematic phase, a small viscosity, a suitable optical anisotropy, a large negative dielectric anisotropy, a high specific resistance, a high stability to ultraviolet light and a high stability to heat. Another aim is to provide a liquid crystal composition has a suitable balance regarding at least two of the characteristics. Another aim is to provide a liquid crystal display device including the composition. Another aim is to provide an AM device having characteristics such as a short response time, a large voltage holding ratio, a low threshold voltage, a large contrast ratio and a long service life.

Solution to Problem

The invention concerns a liquid crystal composition containing at least one compound selected from the group of compounds represented by formula (1) and has a negative dielectric anisotropy, and a liquid crystal display device including the composition:

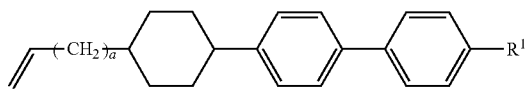

(1)

wherein, in formula (1), $R^1$ is alkyl having 1 to 12 carbons, alkoxy having 1 to 12 carbons, alkenyl having 2 to 12 carbons, or alkenyl having 2 to 12 carbons in which at least one piece of hydrogen is replaced by fluorine; and a is an integer from 0 to 12.

Advantageous Effects of Invention

An advantage of the invention is a liquid crystal composition satisfying at least one of characteristics such as a high maximum temperature of a nematic phase, a low minimum temperature of the nematic phase, a small viscosity, a large optical anisotropy, a large negative dielectric anisotropy, a high specific resistance, a high stability to ultraviolet light and a high stability to heat. Another advantage thereof is a liquid crystal composition has a suitable balance between at least two of the characteristics. Another advantage is a liquid crystal display device includes such a composition. Another advantage is an AM device has characteristics such as a short response time, a large voltage holding ratio, a low threshold voltage, a large contrast ratio and a long service life.

DESCRIPTION OF EMBODIMENTS

Usage of terms herein is as described below. Terms "liquid crystal composition" and "liquid crystal display device" may be occasionally abbreviated as "composition" and "device," respectively. The liquid crystal display device is a generic term for a liquid crystal display panel and a liquid crystal display module. A liquid crystal compound is a generic term for a compound having a liquid crystal phase such as a nematic phase and a smectic phase, and a compound having no liquid crystal phase but to be mixed with a composition for the purpose of adjusting characteristics such as a temperature range of the nematic phase, viscosity and dielectric anisotropy. The compound has a six-membered ring such as 1,4-cyclohexylene and 1,4-phenylene, and rod-like molecular structure. A polymerizable compound is added thereto for the purpose of forming a polymer in the composition.

The liquid crystal composition is prepared by mixing a plurality of liquid crystal compounds. A proportion (content) of the liquid crystal compounds is expressed in terms of weight percent (% by weight) based on the weight of the liquid crystal composition. An additive such as an optically active compound, an antioxidant, an ultraviolet light absorber, a dye, an antifoaming agent, a polymerizable compound, a polymerization initiator and a polymerization inhibitor is added to the composition when necessary. A proportion (content) of the additive is expressed in terms of weight percent (% by weight) based on the weight of the liquid crystal composition in a manner similar to the proportion of the liquid crystal compound. Weight parts per million (ppm) may be occasionally used. A proportion of the polymerization initiator and the polymerization inhibitor is exceptionally expressed based on the weight of the polymerizable compound.

"Maximum temperature of the nematic phase" may be occasionally abbreviated as "maximum temperature." "Minimum temperature of the nematic phase" may be occasionally abbreviated as "minimum temperature." An expression "having a large specific resistance" means that the composition has a large specific resistance at room temperature and also at a temperature close to a maximum temperature of the nematic phase in an initial stage, and the composition has the large specific resistance at room temperature and also at the temperature close to the maximum temperature of the nematic phase even after the device has been used for a long period of time. An expression "having a large voltage holding" means that the device has a large voltage holding ratio at room temperature and also at the temperature close to the maximum temperature of the nematic phase in the initial stage, and the device has the large voltage holding ratio at room temperature and also at the temperature close to the maximum temperature of the nematic phase even after the device has been used for the long period of time. An expression "increase dielectric anisotropy" means that a value of dielectric anisotropy positively increases in a liquid crystal composition having a positive dielectric anisotropy, and the value of dielectric anisotropy negatively increases in a liquid crystal composition having a negative dielectric anisotropy.

An expression "at least 'A' may be replaced by 'B'" means that the number of 'A' is arbitrary. A position of 'A' is arbitrary when the number of 'A' is 1, and also positions thereof can be selected without restriction when the number of 'A' is two or more. A same rule also applies to an expression "at least one piece of 'A' is replaced by 'B'."

In formulas (1) to (5), a symbol such as A, B, C or the like surrounded by a hexagonal shape respectively corresponds to ring A, ring B, ring C or the like. In formula (5), an oblique line crossing the hexagonal shape of ring K means that a connecting position on the ring can be arbitrarily selected by group $P^1$-$Sp^1$. A same rule also applies to group $P^2$-$Sp^2$ of ring L or the like. A subscript such as h represents the number of groups to be bonded with a ring such as ring K. When h is 2, two pieces of $P^1$-$Sp^1$ exist on ring K. Two groups represented by $P^1$-$Sp^1$ may be identical or different, respectively. A same rule also applies to arbitrary two groups when h is larger than 2. A same rule also applies to another group. A compound represented by formula (1) may be occasionally abbreviated as "compound (1)." The abbreviation applies also to a compound represented by formula (2) or the like. Compound (1) means one compound or two or more compounds represented by formula (1). In chemical formulas of component compounds, a symbol of terminal group $R^2$ is used for a plurality of compounds. In the compounds, two groups represented by two pieces of arbitrary $R^2$ may be identical or different. In one case, for example, $R^2$ of compound (2-1) is ethyl and $R^2$ of compound (2-2) is ethyl. In another case, $R^2$ of compound (2-1) is ethyl and $R^2$ of compound (2-2) is propyl. A same rule further applies to a symbol of another terminal group or the like. In formula (2), when b is 2, two pieces of ring A exist. In the compound, two rings represented by two pieces of ring A may be identical or different. A same rule also applies to two pieces of arbitrary ring A when b is larger than 2. A same rule also applies also to symbols such as $Z^1$ and ring D.

Then, 2-fluoro-1,4-phenylene means two divalent groups described below. In a chemical formula, fluorine may be leftward (L) or rightward (R). A same rule also applies to an asymmetrical divalent group such as tetrahydropyran-2,5-diyl.

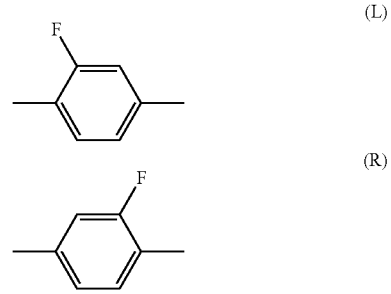

The invention includes the items described below.

Item 1. A liquid crystal composition that has a negative dielectric anisotropy, and contains at least one compound selected from the group of compounds represented by formula (1) as a first component:

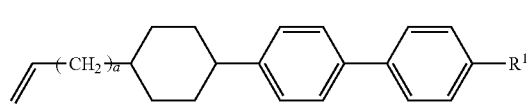

wherein, in formula (1), R is alkyl having 1 to 12 carbons, alkoxy having 1 to 12 carbons, alkenyl having 2 to 12 carbons, or alkenyl having 2 to 12 carbons in which at least one piece of hydrogen is replaced by fluorine; and a is an integer from 0 to 12.

Item 2. The liquid crystal composition according to item 1, wherein a proportion of the first component is in the range of 3% by weight to 30% by weight based on the weight of the liquid crystal composition.

Item 3. The liquid crystal composition according to item 1 or 2, containing at least one compound selected from the group of compounds represented by formula (2) as a second component:

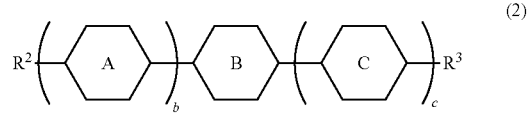

wherein, in formula (2), $R^2$ and $R^3$ are independently alkyl having 1 to 12 carbons, alkoxy having 1 to 12 carbons, alkenyl having 2 to 12 carbons, alkenyloxy having 2 to 12 carbons, alkyl having 1 to 12 carbons in which at least one piece of hydrogen is replaced by fluorine, or alkenyl having 2 to 12 carbons in which at least one piece of hydrogen is replaced by fluorine; ring A and ring C are independently 1,4-cyclohexylene, 1,4-cyclohexenylene, 1,4-phenylene, 1,4-phenylene in which at least one piece of hydrogen is replaced by fluorine or chlorine, or tetrahydropyran-2,5-diyl; ring B is 2,3-difluoro-1,4-phenylene, 2-chloro-3-fluoro-1,4-phenylene, 2,3-difluoro-5-methyl-1,4-phenylene, 3,4,5-trifluoronaphthalene-2,6-diyl or 7,8-difluorochroman-2,6-diyl; b is 1, 2 or 3; c is 0 or 1; and a sum of b and c is 3 or less.

Item 4. The liquid crystal composition according to any one of items 1 to 3, containing at least one compound selected from the group of compounds represented by formulas (2-1) to (2-11) as the second component:

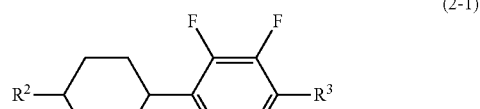

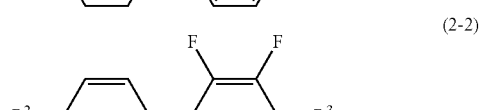

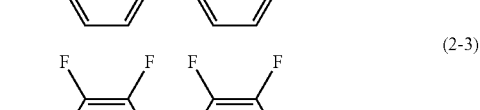

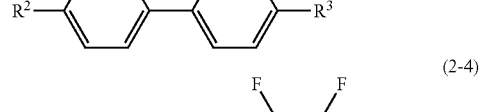

(2-5)

(2-6)

(2-7)

(2-8)

(2-9)

(2-10)

(2-11)

wherein, in formulas (2-1) to (2-11), $R^2$ and $R^3$ are independently alkyl having 1 to 12 carbons, alkoxy having 1 to 12 carbons, alkenyl having 2 to 12 carbons, alkenyloxy having 2 to 12 carbons, alkyl having 1 to 12 carbons in which at least one piece of hydrogen is replaced by fluorine, or alkenyl having 2 to 12 carbons in which at least one piece of hydrogen is replaced by fluorine.

Item 5. The liquid crystal composition according to item 3 or 4, wherein a proportion of the second component is in the range of by weight to 70% by weight based on the weight of the liquid crystal composition.

Item 6. The liquid crystal composition according to any one of items 1 to 5, further containing at least one compound selected from the group of compounds represented by formula (3) as a third component:

(3)

$$R^4 \left( \boxed{D} - Z^1 \right)_d \boxed{E} - Z^2 - \boxed{F} - R^5$$

wherein, in formula (3), $R^4$ and $R^5$ are independently alkyl having 1 to 12 carbons, alkoxy having 1 to 12 carbons, alkenyl having 2 to 12 carbons, alkyl having 1 to 12 carbons in which at least one piece of hydrogen is replaced by fluorine, or alkenyl having 2 to 12 carbons in which at least one piece of hydrogen is replaced by fluorine; ring D, ring E and ring F are independently 1,4-cyclohexylene, 1,4-phenylene, 2-fluoro-1,4-phenylene or 2,5-difluoro-1,4-phenylene; $Z^1$ and $Z^2$ are independently a single bond, —CH$_2$CH$_2$—, —CH$_2$O—, —OCH$_2$—, —COO— or —OCO—; d is 0, 1 or 2; in which ring E is 1,4-cyclohexylene, 2-fluoro-1,4-phenylene or 2,5-difluoro-1,4-phenylene when d is 1.

Item 7. The liquid crystal composition according to any one of items 1 to 6, containing at least one compound selected from the group of compounds represented by formulas (3-1) to formula (3-12) as the third component:

(3-1)

(3-2)

(3-3)

(3-4)

(3-5)

(3-6)

(3-7)

(3-8)

(3-9)

-continued

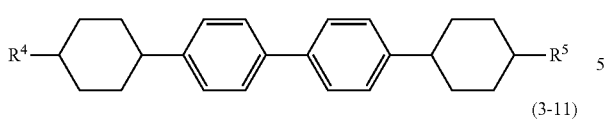
(3-10)

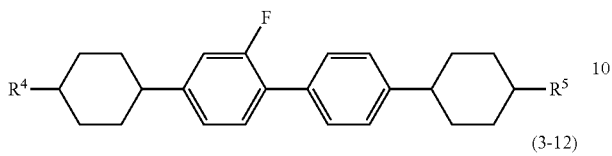
(3-11)

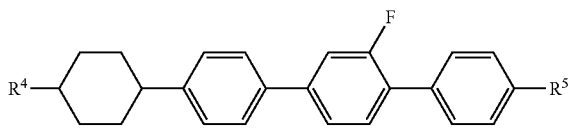
(3-12)

wherein, in formulas (3-1) to (3-12), $R^4$ and $R^5$ are independently alkyl having 1 to 12 carbons, alkoxy having 1 to 12 carbons, alkenyl having 2 to 12 carbons, alkyl having 1 to 12 carbons in which at least one piece of hydrogen is replaced by fluorine, or alkenyl having 2 to 12 carbons in which at least one piece of hydrogen is replaced by fluorine.

Item 8. The liquid crystal composition according to item 6 or 7, wherein a proportion of the third component is in the range of 10% by weight to 90% by weight based on the weight of the liquid crystal composition.

Item 9. The liquid crystal composition according to any one of items 1 to 8, containing at least one compound selected from the group of compounds represented by formula (4) as a fourth component:

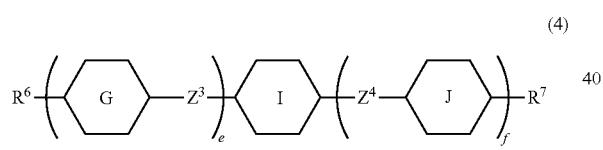
(4)

wherein, in formula (4), $R^6$ and $R^7$ are independently alkyl having 1 to 12 carbons, alkoxy having 1 to 12 carbons, alkenyl having 2 to 12 carbons, alkenyloxy having 2 to 12 carbons, alkyl having 1 to 12 carbons in which at least one piece of hydrogen is replaced by fluorine, or alkenyl having 2 to 12 carbons in which at least one piece of hydrogen is replaced by fluorine; ring G and ring J are independently 1,4-cyclohexylene, 1,4-cyclohexenylene, 1,4-phenylene, 1,4-phenylene in which at least one piece of hydrogen is replaced by fluorine or chlorine, or tetrahydropyran-2,5-diyl; ring I is 2,3-difluoro-1,4-phenylene, 2-chloro-3-fluoro-1,4-phenylene, 2,3-difluoro-5-methyl-1,4-phenylene, 3,4,5-trifluoronaphthalene-2,6-diyl or 7,8-difluorochroman-2,6-diyl; $Z^3$ and $Z^4$ are independently a single bond, —CH$_2$CH$_2$—, —CH$_2$O—, —OCH$_2$—, —COO— or —OCO—; at least one of $Z^3$ and $Z^4$ is —CH$_2$CH$_2$—, —CH$_2$O—, OCH$_2$—COO— or —OCO—; e is 1, 2 or 3; f is 0 or 1; and a sum of e and f is 3 or less.

Item 10. The liquid crystal composition according to any one of items 1 to 9, containing at least one compound selected from the group of compounds represented by formulas (4-1) to (4-8) as the fourth component:

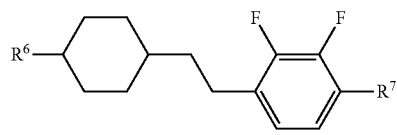
(4-1)

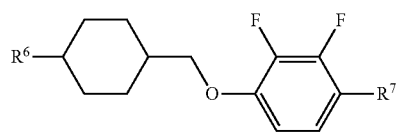
(4-2)

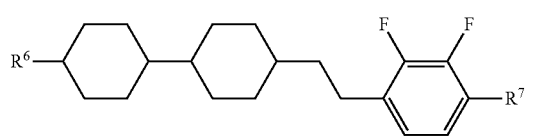
(4-3)

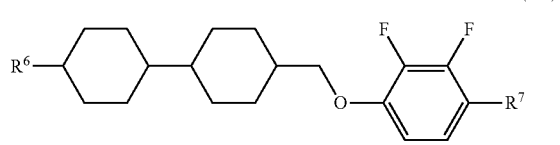
(4-4)

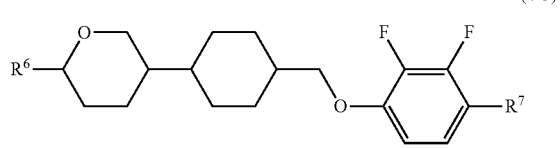
(4-5)

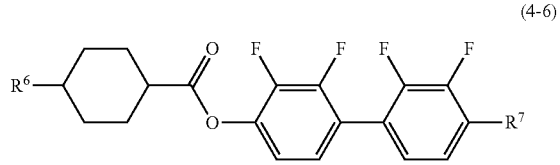
(4-6)

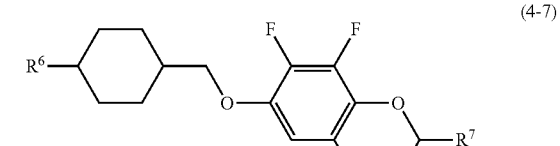
(4-7)

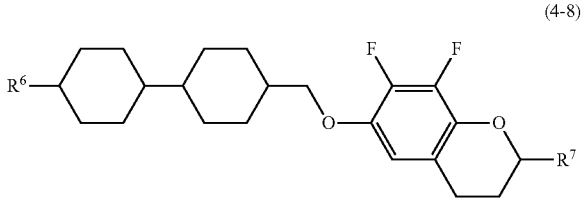
(4-8)

wherein, in formulas (4-1) to (4-8), $R^6$ and $R^7$ are independently alkyl having 1 to 12 carbons, alkoxy having 1 to 12 carbons, alkenyl having 2 to 12 carbons, alkenyloxy having 2 to 12 carbons, alkyl having 1 to 12 carbons in which at least one piece of hydrogen is replaced by fluorine, or alkenyl having 2 to 12 carbons in which at least one piece of hydrogen is replaced by fluorine.

Item 11. The liquid crystal composition according to item 9 or 10, wherein a proportion of the fourth component is in the range of 5% by weight to 60% by weight based on the weight of the liquid crystal composition.

Item 12. The liquid crystal composition according to any one of items 1 to 11, containing at least one polymerizable compound selected from the group of compounds represented by formula (5) as an additive component:

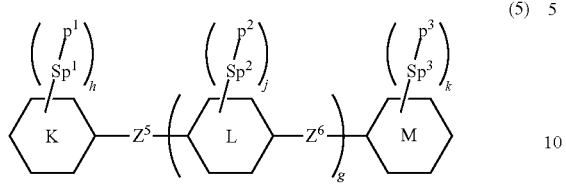
(5)

wherein, in formula (5), ring K and ring M are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one piece of hydrogen may be replaced by halogen, alkyl having 1 to 12 carbons, alkoxy having 1 to 12 carbons, or alkyl having 1 to 12 carbons in which at least one piece of hydrogen was replaced by halogen; ring L is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one piece of hydrogen may be replaced by halogen, alkyl having 1 to 12 carbons, alkoxy having 1 to 12 carbons, or alkyl having 1 to 12 carbons in which at least one piece of hydrogen is replaced by halogen; $Z^5$ and $Z^6$ are independently a single bond or alkylene having 1 to 10 carbons, and in the alkylene, at least one piece of —$CH_2$— may be replaced by —O—, —CO—, —COO— or —OCO—, at least one piece of —$CH_2$—$CH_2$— may be replaced by —CH=CH—, —C($CH_3$)=CH—, —CH=C($CH_3$)— or —C($CH_3$)=C($CH_3$)—, and in the groups, at least one piece of hydrogen may be replaced by fluorine or chlorine; $P^1$, $P^2$ and $P^3$ are independently a polymerizable group; $Sp^1$, $Sp^2$ and $Sp^3$ are independently a single bond or alkylene having 1 to 10 carbons, and in the alkylene, at least one piece of —$CH_2$— may be replaced by —O—, —COO—, —OCO— or —OCOO—, at least one piece of —$CH_2$—$CH_2$— may be replaced by —CH=CH— or —C≡C—, and in the groups, at least one piece of hydrogen may be replaced by fluorine or chlorine; g is 0, 1 or 2; h, j and k are independently 0, 1, 2, 3 or 4; and a sum of h, j and k is 1 or more.

Item 13. The liquid crystal composition according to item 12, wherein, in formula (5) described in item 12, $P^1$, $P^2$ and $P^3$ are independently a polymerizable group selected from the group of groups represented by formulas (P-1) to (P-6):

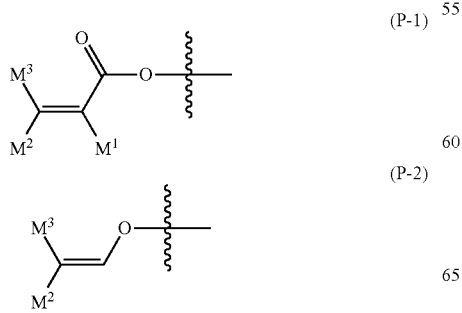

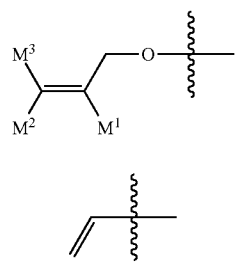
(P-3)

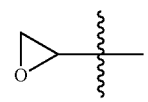
(P-4)

(P-5)

(P-6)

wherein, in formulas (P-1) to (P-6), $M^1$, $M^2$ and $M^3$ are independently hydrogen, fluorine, alkyl having 1 to 5 carbons, or alkyl having 1 to 5 carbons in which at least one piece of hydrogen is replaced by halogen; and when both $P^1$ and $P^3$ are a group represented by formula (P-4), in formula (5), at least one of $Sp^1$ and $Sp^3$ is alkylene in which at least one piece of —$CH_2$— is replaced by —O—, —COO—, —OCO— or —OCOO—.

Item 14. The liquid crystal composition according to any one of items 1 to 13, containing at least one polymerizable compound selected from the group of compounds represented by formulas (5-1) to (5-27) as the additive component:

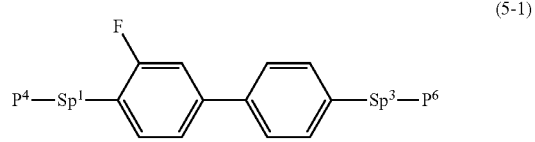
(5-1)

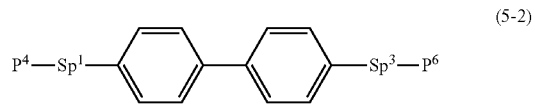
(5-2)

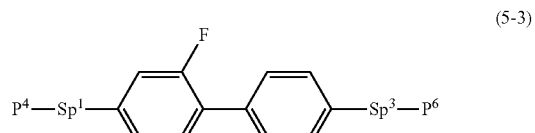
(5-3)

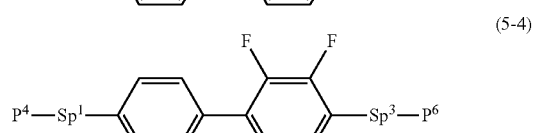
(5-4)

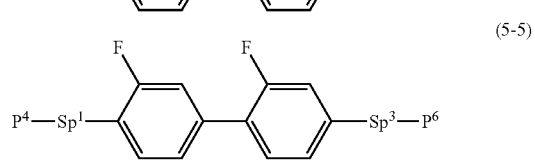
(5-5)

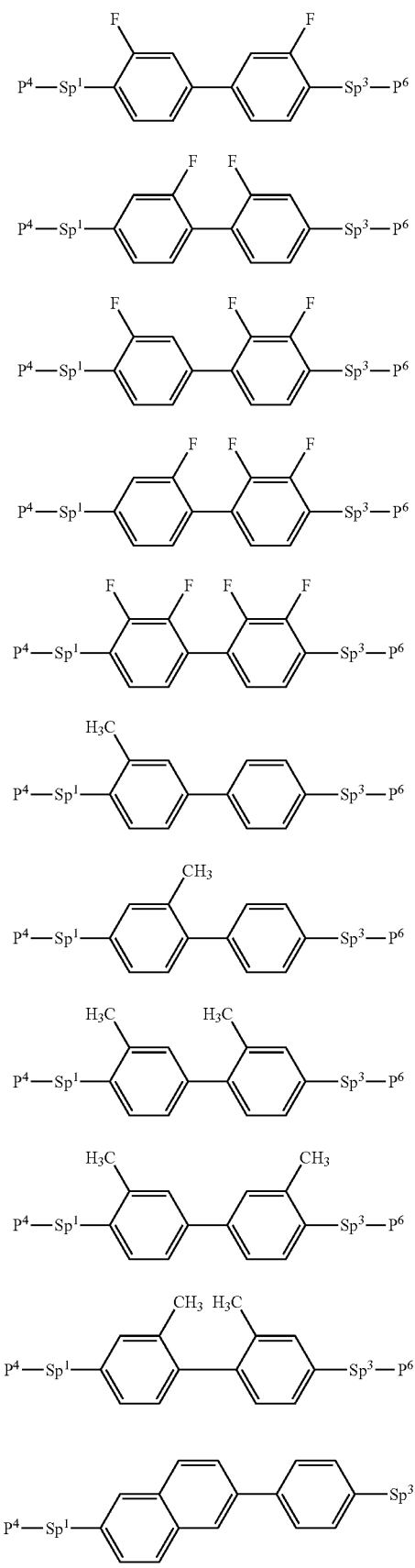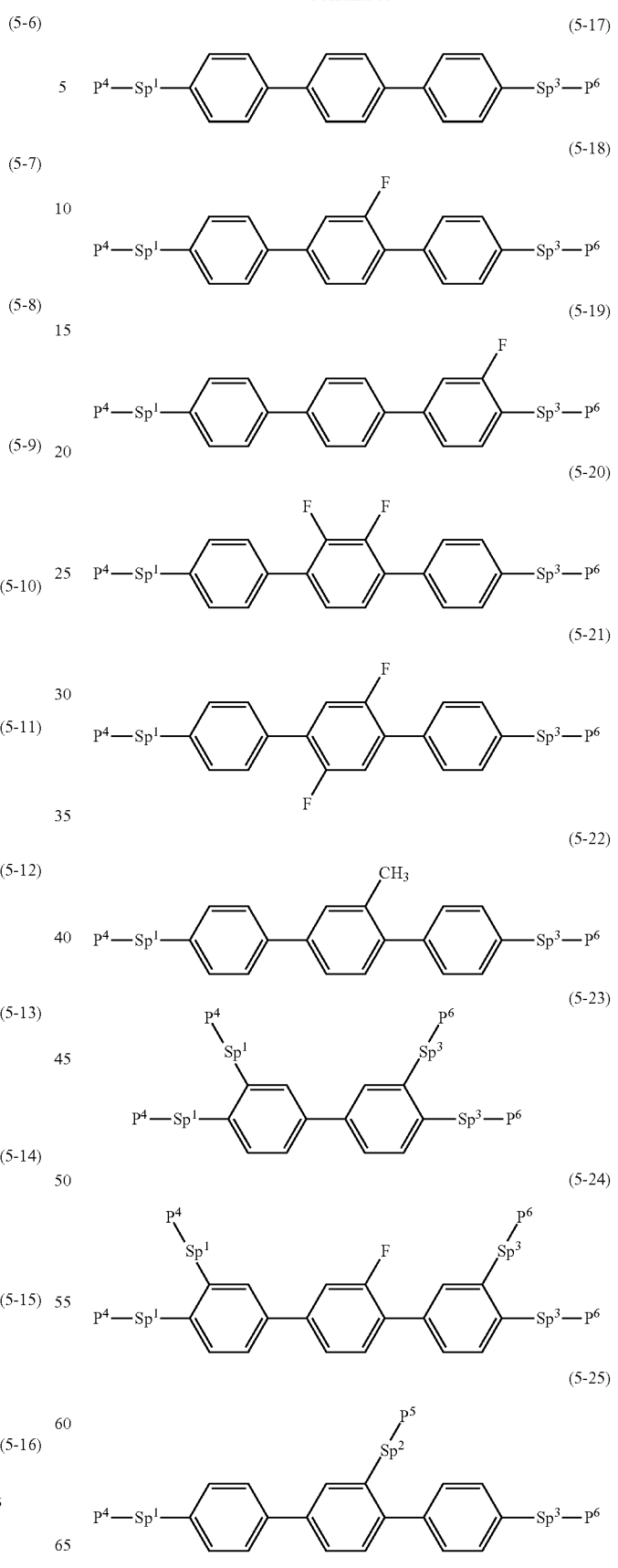

(5-26)

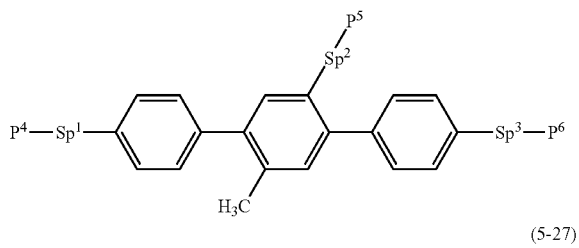

(5-27)

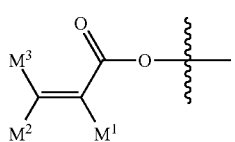

wherein, in formulas (5-1) to (5-27), $P^4$, $P^5$ and $P^6$ are independently a polymerizable group selected from the group of groups represented by formulas (P-1) to (P-3):

(P-1)

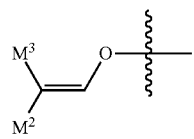

(P-2)

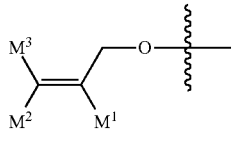

(P-3)

wherein, in formulas (P-1) to (P-3), $M^1$, $M^2$ and $M^3$ are independently hydrogen, fluorine, alkyl having 1 to 5 carbons, or alkyl having 1 to 5 carbons in which at least one piece of hydrogen is replaced by halogen; and in formulas (5-1) to (5-27), $Sp^1$, $Sp^2$ and $Sp^3$ are independently a single bond or alkylene having 1 to 10 carbons, and in the alkylene, at least one piece of —$CH_2$— may be replaced by —O—, —COO—, —OCO— or —OCOO—, at least one piece of —$CH_2$—$CH_2$— may be replaced by —CH=CH— or —C≡O—, and in the groups, at least one piece of hydrogen may be replaced by fluorine or chlorine.

Item 15. The liquid crystal composition according to any one of items 12 to 14, wherein a proportion of the additive component is in the range of 0.03% by weight to 10% by weight based on the weight of the liquid crystal composition.

Item 16. A liquid crystal display device including the liquid crystal composition according to any one of items 1 to 15.

Item 17. The liquid crystal display device according to item 16, wherein an operating mode in the liquid crystal display device is an IPS mode, a VA mode, an FFS mode or an FPA mode, and a driving mode in the liquid crystal display device is an active matrix mode.

Item 18. A liquid crystal display device having a polymer sustained alignment mode, wherein the liquid crystal display device includes the liquid crystal composition according to any one of items to 15, and a polymerizable compound in the liquid crystal composition is polymerized.

Item 19. Use of the liquid crystal composition according to any one of items 1 to 15 in a liquid crystal display device.

Item 20. Use of the liquid crystal composition according to any one of items 12 to 15 in a polymer sustained alignment mode liquid crystal display device.

The invention further includes the following items: (a) the composition containing at least one additive such as an optically active compound, an antioxidant, an ultraviolet light absorber, a dye, an antifoaming agent, a polymerization initiator and a polymerization inhibitor; (b) an AM device including the composition; (c) an AM device including the composition further containing a polymerizable compound, and having a polymer sustained alignment (PSA) mode; (d) a polymer sustained alignment (PSA) mode n AM device including the composition in which a polymerizable compound is polymerized; (f) a device including the composition and having a TN mode, an ECB mode, an OCB mode, an IPS mode, an FFS mode or an FPA mode; (g) a transmissive device including the composition; (g) use of the composition as a composition having the nematic phase; and (h) use of an optically active composition by adding the optically active compound to the composition.

The composition of the invention will be described. First, a constitution of component compounds in the composition will be described. Second, main characteristics of the component compounds and main effects of the compounds on the composition will be described. Third, a combination of components in the composition, a preferred proportion of the components and a basis thereof will be described. Fourth, a preferred embodiment of the component compounds will be described. Fifth, preferred component compounds will be described. Sixth, an additive may be mixed with the composition will be described. Seventh, methods for synthesizing the component compounds will be described. Last, an application of the composition will be described.

First, the constitution of component compounds in the composition will be described. The composition of the invention is classified into composition A and composition B. Composition A may further contain any other liquid crystal compound, any other additive or the like in addition to the liquid crystal compound selected from compound (1), compound (2), compound (3), compound (4) and compound (5). "Any other liquid crystal compound" means a liquid crystal compound different from compound (1), compound (2), compound (3) and compound (4). Such a compound is mixed with the composition for the purpose of further adjusting the characteristics. The additive is the optically active compound, the antioxidant, the ultraviolet light absorber, the dye, the antifoaming agent, the polymerizable compound, the polymerization initiator, the polymerization inhibitor or the like.

Composition B consists essentially of compounds selected from compound (1), compound (2), compound (3), compound (4) and compound (5). "Essentially" means that the composition may contain an additive, but does not contain no any other liquid crystal compound. Composition B has a smaller number of components than composition A has. Composition B is preferred to composition A in view of cost reduction. Composition A is preferred to composition B in view of possibility of further adjusting physical properties by mixing any other liquid crystal compound.

Second, the main characteristics of the component compounds and the main effects of the compounds on the characteristics of the composition are described. The main characteristics of the component compounds are summarized in Table 2 on a basis of advantageous effects of the invention. In Table 2, a symbol L stands for "large" or "high," a symbol M stands for "medium" and a symbol S stands for "small" or "low." The symbols L, M and S represent a classification based on a qualitative comparison among the component compounds, and 0 (zero) stands for "a value is zero or nearly zero."

TABLE 2

Characteristics of Compounds

| | Compounds | | | |
|---|---|---|---|---|
| | (1) | (2) | (3) | (4) |
| Maximum temperature | M | S to M | S to L | S to M |
| Viscosity | M | L | S to M | L |
| Optical anisotropy | M | M to L | S to L | M to L |
| Dielectric anisotropy | 0 | L[1)] | 0 | L[1)] |
| Specific resistance | L | L | L | L |

[1)]A value of dielectric anisotropy is negative, and the symbol shows magnitude of an absolute value.

Upon mixing the component compounds with the composition, the main effects of the component compounds on the characteristics of the composition are as described below. Compound (1) increases the maximum temperature and decreases the minimum temperature. Compound (2) increases dielectric anisotropy and decreases the minimum temperature. Compound (3) decreases viscosity or increases the maximum temperature. Compound (4) increases the dielectric anisotropy and decreases the minimum temperature. Compound (5) gives the polymer by polymerization, and the polymer shortens a response time in the device, and improves image persistence.

Third, the combination of components in the composition, the preferred proportion of the components and the basis thereof will be described. The preferred combination of components in the composition includes a combination of the first component and the second component, a combination of the first component and the third component, a combination of the first component and the fourth component, a combination of the first component and the additive, a combination of the first component, the second component and the third component, a combination of the first component, the second component and the fourth component, a combination of the first component, the second component and the additive component, a combination of the first component, the third component and the fourth component, a combination of the first component, the third component and the additive component, a combination of the first component, the fourth component and the additive component, a combination of the first component, the second component, the third component and the fourth component, a combination of the first component, the second component, the third component and the additive component, a combination of the first component, the second component, the fourth component and the additive component, a combination of the first component, the third component, the fourth component and the additive component, or a combination of the first component, the second component, the third component, the fourth component and the additive component. A further preferred combination is the combination of the first component, the second component and the third component, the combination of the first component, the second component, the third component and the fourth component, the combination of the first component, the second component, the third component and the additive component, or the combination of the first component, the second component, the third component, the fourth component and the additive component.

A preferred proportion of the first component is about 3% by weight or more, based thereon, for increasing the maximum temperature, and about 30% by weight or less for decreasing the minimum temperature. A further preferred proportion is in the range of about 5% by weight to 25% by weight based thereon. A particularly preferred proportion is in the range of about 5% by weight to 20% by weight based thereon.

A preferred proportion of the second component is about 5% by weight or more, based thereon, for increasing the dielectric anisotropy, and about 70% by weight or less for decreasing the minimum temperature. A further preferred proportion is in the range of about 10% by weight to 65% by weight based thereon. A particularly preferred proportion is in the range of about 15% by weight to 60% by weight based thereon.

A preferred proportion of the third component is about 10% by weight or more for increasing the maximum temperature or decreasing viscosity, and about 90% by weight or less for increasing the dielectric anisotropy. A further preferred proportion is in the range of about 20% by weight to 80% by weight based thereon. A particularly preferred proportion is in the range of about 30% by weight to 70% by weight based thereon.

A preferred proportion of the fourth component is about 5% by weight or more for increasing the dielectric anisotropy, and about 60% by weight or less for decreasing the minimum temperature. A further preferred proportion is in the range of about 10% by weight to 50% by weight based thereon. A particularly preferred proportion is in the range of about 10% by weight to 40% by weight based thereon.

Compound (5) is mixed with the composition to be adapted to the device having the polymer sustained alignment mode. A preferred proportion of the additive is about 0.03% by weight or more for aligning liquid crystal molecules, and about 10% by weight or less for preventing a poor display in the device, based on the weight of the liquid crystal composition. A further preferred proportion of the additive is in the range of about 0.1% by weight to 2% by weight based thereon. A particularly preferred proportion of the additive is in the range of about 0.2% by weight to 1.0% by weight based thereon.

Fourth, the preferred embodiment of the component compounds will be described. In formula (1), formula (2), formula (3) and formula (4), $R^1$ is alkyl having 1 to 12 carbons, alkoxy having 1 to 12 carbons, alkenyl having 2 to 12 carbons, or alkenyl having 2 to 12 carbons in which at least one piece of hydrogen is replaced by fluorine. Preferred $R^1$ is alkyl having 1 to 12 carbons for increasing stability. $R^2$, $R^3$, $R^6$ and $R^7$ are independently alkyl having 1 to 12 carbons, alkoxy having 1 to 12 carbons, alkenyl having 2 to 12 carbons, alkenyloxy having 2 to 12 carbons, alkyl having 1 to 12 carbons in which at least one piece of hydrogen is replaced by fluorine, or alkenyl having 2 to 12 carbons in which at least one piece of hydrogen is replaced by fluorine. Preferred $R^2$, $R^3$, $R^6$ or $R^7$ is alkyl having 1 to 12 carbons for increasing the stability, or alkoxy having 1 to 12 carbons for increasing the dielectric anisotropy. $R^4$ and $R^6$ are independently alkyl having 1 to 12 carbons, alkoxy having 1 to 12 carbons, alkenyl having 2 to 12 carbons, alkyl having 1 to 12 carbons in which at least one piece of hydrogen is replaced by fluorine, or alkenyl having 2 to 12 carbons in which at least one piece of hydrogen is replaced by fluorine. Preferred $R^4$ or $R^5$ is alkenyl having 2 to 12 carbons for decreasing the viscosity, or alkyl having 1 to 12 carbons for increasing the stability.

Preferred alkyl is methyl, ethyl, propyl, butyl, pentyl, hexyl, heptyl or octyl. Further preferred alkyl is ethyl, propyl, butyl, pentyl or heptyl for decreasing the viscosity.

Preferred examples of alkenyl in which at least one piece of hydrogen is replaced by fluorine include fluoromethyl, 2-fluoroethyl, 3-fluoropropyl, 4-fluorobutyl, 5-fluoropentyl, 6-fluorohexyl, 7-fluoroheptyl or 8-fluorooctyl. Further preferred examples include 2-fluoroethyl, 3-fluoropropyl, 4-fluorobutyl or 5-fluoropentyl for increasing the dielectric anisotropy.

Preferred alkoxy is methoxy, ethoxy, propoxy, butoxy, pentyloxy, hexyloxy or heptyloxy. Further preferred alkoxy is methoxy or ethoxy for decreasing the viscosity.

Preferred alkenyl is vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl or 5-hexenyl. Further preferred alkenyl is vinyl, 1-propenyl, 3-butenyl or 3-pentenyl for decreasing the viscosity. A preferred configuration of —CH═CH— in alkenyl depends on a position of a double bond. Trans is preferred in alkenyl such as 1-propenyl, 1-butenyl, 1-pentenyl, 1-hexenyl, 3-pentenyl and 3-hexenyl for decreasing the viscosity or the like. Cis is preferred in alkenyl such as 2-butenyl, 2-pentenyl and 2-hexenyl. In the alkenyl, straight-chain alkenyl is preferred to branched-chain alkenyl.

Preferred alkenyloxy is vinyloxy, allyloxy, 3-butenyloxy, 3-pentenyloxy or 4-pentenyloxy. Further preferred alkenyloxy is allyloxy or 3-butenyloxy for decreasing the viscosity.

Preferred examples of alkenyl in which at least one piece of hydrogen is replaced by fluorine include 2,2-difluorovinyl, 3,3-difluoro-2-propenyl, 4,4-difluoro-3-butenyl, 5,5-difluoro-4-pentenyl or 6,6-difluoro-5-hexenyl. Further preferred examples include 2,2-difluorovinyl or 4,4-difluoro-3-butenyl for decreasing the viscosity.

Ring A, ring C, ring G and ring J are independently 1,4-cyclohexylene, 1,4-cyclohexenylene, 1,4-phenylene, 1,4-phenylene in which at least one piece of hydrogen is replaced by fluorine or chlorine or tetrahydropyran-2,5-diyl. Preferred examples of 1,4-phenylene in which at least one piece of hydrogen is replaced by fluorine or chlorine include 2-fluoro-1,4-phenylene, 2,3-difluoro-1,4-phenylene or 2-chloro-3-fluoro-1,4-phenylene. Preferred ring A, ring C, ring G or ring J is 1,4-cyclohexylene for decreasing the viscosity, tetrahydropyran-2,5-diyl for increasing the dielectric anisotropy, or 1,4-phenylene for increasing optical anisotropy. According to the configuration of 1,4-cyclohexylene, trans is preferred to cis for increasing the maximum temperature. Tetrahydropyran-2,5-diyl includes:

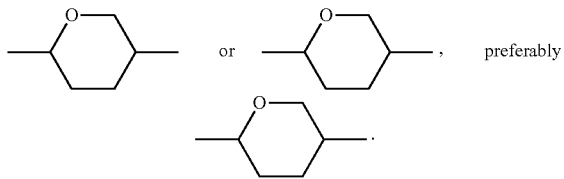

or , preferably

Ring B and ring I are independently 2,3-difluoro-1,4-phenylene, 2-chloro-3-fluoro-1,4-phenylene, 2,3-difluoro-5-methyl-1,4-phenylene, 3,4,5-trifluoronaphthalene-2,6-diyl or 7,8-difluorochroman-2,6-diyl. Preferred ring B or ring I is 2,3-difluoro-1,4-phenylene for decreasing the viscosity, 2-chloro-3-fluoro-1,4-phenylene for decreasing the optical anisotropy or 7,8-difluorochroman-2,6-diyl for increasing the dielectric anisotropy.

Ring D, ring E and ring F are independently 1,4-cyclohexylene, 1,4-phenylene, 2-fluoro-1,4-phenylene or 2,5-difluoro-1,4-phenylene. Preferred ring D, ring E or ring F is 1,4-cyclohexylene for decreasing the viscosity or for increasing the maximum temperature, or 1,4-phenylene for decreasing the minimum temperature.

$Z^1$ and $Z^2$ are independently a single bond, —CH$_2$CH$_2$—, —CH$_2$O—, —OCH$_2$—, —COO— or —OCO—. Preferred $Z^1$ or $Z^2$ is a single bond for increasing the stability. $Z^3$ and $Z^4$ are independently a single bond, —CH$_2$CH$_2$—, —CH$_2$O—, —OCH$_2$—, —COO— or —OCO—, and at least one of $Z^3$ and $Z^4$ is —CH$_2$CH$_2$—, —CH$_2$O—, —OCH$_2$—, —COO— or —OCO—. Preferred $Z^3$ or $Z^4$ is a single bond for decreasing the viscosity, —CH$_2$CH$_2$— for decreasing the minimum temperature or —CH$_2$O— for increasing the dielectric anisotropy.

Then, a is an integer from 0 to 12. Preferred a is 0 or 1 for decreasing the viscosity. Then, b is 1, 2 or 3, and c is 0 or 1, and a sum of b and c is 3 or less. Preferred b is 1 for decreasing the viscosity, or 2 or 3 for increasing the maximum temperature. Preferred c is 0 for decreasing the viscosity, or 1 for decreasing the minimum temperature. Then, d is 0, 1 or 2, ring E when is 1 is 1,4-cyclohexylene, 2-fluoro-1,4-phenylene or 2,5-difluoro-1,4-phenylene. Preferred d is 0 for decreasing the viscosity, or 1 or 2 for increasing the maximum temperature. Then, e is 1, 2 or 3, f is 0 or 1, and a sum of e and f is 3 or less. Preferred e is 1 for decreasing the viscosity, or 2 or 3 for increasing the maximum temperature. Preferred f is 0 for decreasing the viscosity, or 1 for decreasing the minimum temperature.

In compound (5), $P^1$, $P^2$ and $P^3$ are a polymerizable group. Preferred $P^1$, $P^2$ or $P^3$ is a polymerizable group selected from the group of groups represented by formulas (P-1) to formula (P-6). Further preferred $P^1$, $P^2$ or $P^3$ is groups (P-1) and (P-2). Particularly preferred group (P-1) is —OCO—CH═CH$_2$ or —OCO—C(CH$_3$)═CH$_2$. A wavy line in groups (P-1) to (P-6) each represents a part in which a bonding is formed.

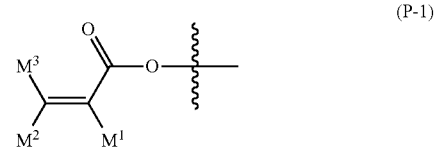
(P-1)

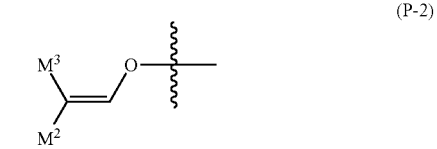
(P-2)

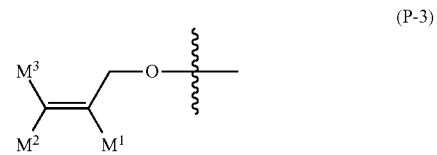
(P-3)

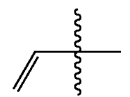

(P-4)

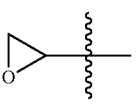

(P-5)

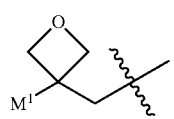

(P-6)

When all of $P^1$, $P^2$ and $P^3$ are group (P-1), $M^1$ (or $M^2$ or $M^3$) in $P^1$, $M^1$ in $P^2$ or $M^1$ in $P^3$ may be identical or different. In groups (P-1) to (P-6), $M^1$, $M^2$ and $M^3$ are independently hydrogen, fluorine, alkyl having 1 to 5 carbons, or alkyl having 1 to 5 carbons in which at least one piece of hydrogen is replaced by halogen. Preferred $M^1$, $M^2$ or $M^3$ is hydrogen or methyl for increasing reactivity. Further preferred $M^1$ is methyl, still further preferred $M^2$ or $M^3$ is hydrogen.

When both $P^1$ and $P^3$ are group (P-4), at least one of $Sp^1$ and $Sp^3$ is alkylene in which at least one piece of —CH$_2$— is replaced by —O—, —COO—, —OCO— or —OCOO—. More specifically, a case where both $P^1$ and $P^3$ are alkenyl such as 1-propenyl is excluded.

$P^4$, $P^5$ and $P^6$ are independently a group represented by formulas (P-1) to (P-3). Preferred $P^4$, $P^5$ or $P^6$ is group (P-1) or (P-2). Further preferred group (P-1) is —OCO—CH═CH$_2$ and —OCO—C(CH$_3$)═CH$_2$. A wavy line in group (P-1) to group (P-3) represents a part to be bonded.

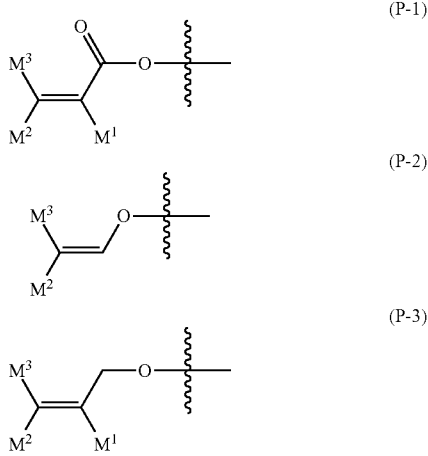

When all of $P^4$, $P^5$ and $P^6$ are group (P-1), $M^1$ (or $M^2$ or $M^3$) in $P^4$, $M^1$ in $P^5$ or $M^1$ in $P^6$ may be identical or different.

$Sp^1$, $Sp^2$ and $Sp^3$ are independently a single bond or alkylene having 1 to 10 carbons, and in the alkylene, at least one piece of —CH$_2$— may be replaced by —O—, —COO—, —OCO— or —OCOO—, at least one piece of —CH$_2$—CH$_2$— may be replaced by —CH═CH— or —C≡C—, and in the groups, at least one piece of hydrogen may be replaced by fluorine or chlorine. Preferred $Sp^1$, $Sp^2$ or $Sp^3$ is a single bond.

Ring K and ring M are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one piece of hydrogen may be replaced by halogen, alkyl having 1 to 12 carbons, alkoxy having 1 to 12 carbons, or alkyl having 1 to 12 carbons in which at least one piece of hydrogen is replaced by halogen. Preferred ring K or ring M is phenyl. Ring L is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one piece of hydrogen may be replaced by halogen, alkyl having 1 to 12 carbons, alkoxy having 1 to 12 carbons, or alkyl having 1 to 12 carbons in which at least one piece of hydrogen is replaced by halogen. Preferred ring L is 1,4-phenylene or 2-fluoro-1,4-phenylene.

$Z^5$ and $Z^6$ are independently a single bond or alkylene having 1 to 10 carbons, and in the alkylene, at least one piece of —CH$_2$— may be replaced by —O—, —CO— —COO— or —OCO—, at least one piece of —CH$_2$—CH$_2$— may be replaced by —CH═CH—, —C(CH$_3$)═CH—, —CH═C(CH$_3$)— or —C(CH$_3$)═C(CH$_3$)—, and in the groups, at least one piece of hydrogen may be replaced by fluorine or chlorine. Preferred $Z^5$ or $Z^6$ is a single bond, —CH$_2$CH$_2$—, —CH$_2$O—, —OCH$_2$—, —COO— or —OCO—. Further preferred $Z^5$ or $Z^6$ is a single bond.

Then, g is 0, 1 or 2. Preferred g is 0 or 1. Then, h, j and k are independently 0, 1, 2, 3 or 4, and a sum of h, j and k is 1 or more. Preferred h, j or k is 1 or 2.

Fifth, the preferred component compounds will be described. Preferred compound (2) includes compounds (2-1) to compound (2-11) described in item 4. In the compounds, at least one of the second components is preferably compound (2-1), compound (2-2), compound (2-4) or compound (2-8). A combination of at least two of the second components is preferably a combination of compound (2-1) and compound (2-4) or a combination of compound (2-1) and compound (2-8).

Preferred compound (3) includes compounds (3-1) to (3-12) described in item 7. In the compounds, at least one of the third components is preferably compound (3-1), compound (3-3), compound (3-5), compound (3-6) or compound (3-7). A combination of at least two of the third components is preferably a combination of compound (3-1) and compound (3-3) or a combination of compound (3-1) and compound (3-5).

Preferred compound (4) includes compounds (4-1) to (4-8) described in item 10. In the compounds, at least one of the fourth components is preferably compound (4-1), compound (4-2), compound (4-4), compound or compound (4-8). A combination of at least two of the fourth components is preferably a combination of compound (4-2) and compound (4-4).

Preferred compound (5) includes compounds (5-1) to (5-27) described in item 14. In the compounds, at least one of the additive components is preferably compound (5-1), compound (5-2), compound (5-24), compound (5-25), compound (5-26) or compound (5-27). A combination of at least two of the additive components is preferably a combination of compounds (5-1) and (5-2), a combination of compounds (5-1) and (5-18), a combination of compounds (5-2) and (5-24), a combination of compounds (5-2) and (5-25), a combination of compounds (5-2) and (5-26), a combination of compounds (5-25) and (5-26), or a combination of compounds (5-18) and (5-24). In groups (P-1) to (P-3), preferred $M^1$, $M^2$ or $M^3$ is hydrogen or methyl. Preferred $Sp^1$, $Sp^2$ or $Sp^3$ is a single bond, —$CH_2CH_2$—, —$CH_2O$—, —$OCH_2$—, —COO—, —OCO—, —CO—CH=CH— or —CH=CH—CO—.

Sixth, the additive that may be mixed with the composition will be described. The additive is the optically active compound, the antioxidant, the ultraviolet light absorber, the dye, the antifoaming agent, the polymerizable compound, the polymerization initiator, the polymerization inhibitor or the like. The optically active compound is mixed with the composition for inducing a helical structure in liquid crystal molecules to give a twist angle. Examples of the compound are compounds (6-1) to (6-5). A preferred proportion of the optically active compound is about 5% by weight or less. A further preferred proportion is in the range of about 0.01% by weight to 2% by weight.

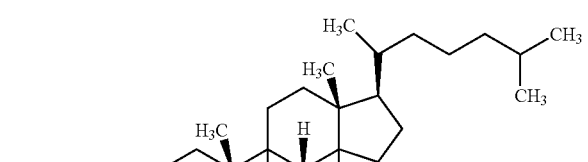
(6-1)

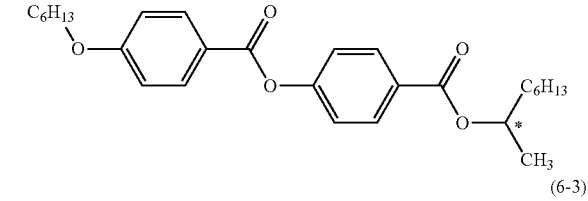
(6-2)

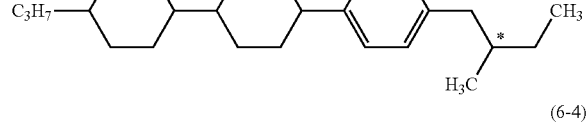
(6-3)

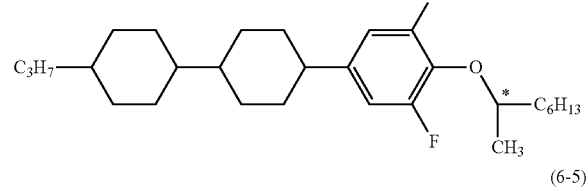
(6-4)

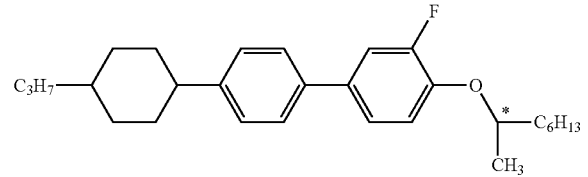
(6-5)

The antioxidant is mixed with the composition for preventing a decrease in the specific resistance caused by being heated in air, or for maintaining the large voltage holding ratio at room temperature and also at a temperature close to the maximum temperature of the nematic phase after the device has been used for a long period of time. Preferred examples of the antioxidant includes compound (7) where n is an integer from 1 to 9.

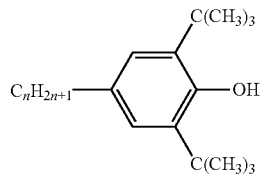
(7)

Preferred n in compound (7) is 1, 3, 5, 7 or 9. Further preferred n is 7. Compound (7) where n is 7 is effective for maintaining the large voltage holding ratio at room temperature and also at the temperature close to the maximum temperature of the nematic phase after the device has been used for a long period of time because the above compound (7) has a small volatility. A preferred proportion of the antioxidant is about 50 ppm or more for achieving an effect thereof, and about 600 ppm or less for avoiding a decrease in the maximum temperature or an increase in the minimum temperature. A further preferred proportion is in the range of about 100 ppm to 300 ppm.

Preferred examples of the ultraviolet light absorber include a benzophenone derivative, a benzoate derivative and a triazole derivative. A light stabilizer such as amine having steric hindrance is preferred. A preferred proportion of the absorber or the stabilizer is about 50 ppm or more for achieving an effect thereof, and about 1000 ppm or less for avoiding a decrease in the maximum temperature. A further preferred proportion is in the range of about 100 ppm to 10,000 ppm.

A dichroic dye such as an azo dye or an anthraquinone dye is mixed with the composition to be adapted to a device having a guest host (GH) mode. A preferred proportion of the dye is in the range of about 0.01% by weight to 10% by weight. An antifoaming agent such as dimethyl silicone oil or methyl phenyl silicone oil is mixed with the composition for preventing foam formation. A preferred proportion of the antifoaming agent is about 1 ppm or more for achieving an effect thereof, and about 1,000 ppm or less for avoiding a poor display. A further preferred proportion is in the range of about 1 ppm to 500 ppm.

The polymerizable compound is used to be adapted to a device having a polymer sustained alignment (PSA) mode. Compound (5) is suitable for the purpose. A polymerizable compound different from compound (5) may be mixed with the composition together with compound (5). Preferred examples of such a polymerizable compound include a compound such as acrylate, methacrylate, a vinyl compound, a vinyloxy compound, propenyl ether, an epoxy compound (oxirane, oxetane) and vinyl ketone. Further preferred examples include a derivative of acrylate or methacrylate. A preferred proportion of compound (5) is 10% by weight or more based on the total weight of the polymerizable compound. A further preferred proportion is 50% by weight or more. A particularly preferred proportion is 80% by weight or more. A most preferred proportion is 100% by weight.

The polymerizable compound such as compound (5) is polymerized by irradiation with ultraviolet light. The polymerizable compound may be polymerized in the presence of a suitable initiator such as a photopolymerization initiator. Suitable conditions for polymerization, suitable types of the initiator and suitable amounts thereof are known to those skilled in the art and are described in literature. For example, Irgacure 651 (registered trademark; BASF), Irgacure 184 (registered trademark; BASF) or Darocur 1173 (registered trademark; BASF), each being a photoinitiator, is suitable for radical polymerization. A preferred proportion of the photopolymerization initiator is in the range of about 0.1% by weight to 5% by weight based on the total weight of the polymerizable compound. A further preferred proportion is in the range of about 1% by weight to 3% by weight.

Upon storing the polymerizable compound such as compound (5) the polymerization inhibitor may be added thereto. The polymerizable compound is ordinarily added to the composition without removing the polymerization inhibitor. Examples of the polymerization inhibitor include hydroquinone and a hydroquinone derivative such as methylhydroquinone, 4-tert-butylcatechol, 4-methoxyphenol and phenothiazine.

Seventh, the methods for synthesizing the component compounds will be described. The compounds are synthesized by known methods. Examples of the synthetic methods are described. Compound (1) is synthesized by a method described to JP S59-176221 A. Compound (2-1) is synthesized by a method described to JP 2000-053602 A. Compound (3-1) is synthesized by a method described in JP S59-176221 A. Compound (3-12) is synthesized by a method described in JP H2-237949 A. Compound (4-1) is synthesized by a method described in JP H2-503441 A. A compound where t in formula (7) is 1 can be obtained from Sigma-Aldrich Corporation. Compound (7) where n is 7 or the like can be synthesized according to a method described to U.S. Pat. No. 3,660,505 B.

Any compounds whose synthetic methods are not described can be prepared according to methods described in books such as Organic Syntheses (John Wiley & Sons, Inc.), Organic Reactions (John Wiley & Sons, Inc.), Comprehensive Organic Synthesis (Pergamon Press) and New Experimental Chemistry Course (Shin Jikken Kagaku Koza in Japanese) (Maruzen Co., Ltd.). The composition is prepared according to publicly known methods using the thus obtained compounds. For example, the component compounds are mixed and dissolved in each other by heating.

Last, the application of the composition will be described. The composition of the invention mainly has a minimum temperature of about −10° C. or lower, a maximum temperature of about 70° C. or higher, and the optical anisotropy in the range of about 0.07 to 0.20. A device including the composition has the large voltage holding ratio. The composition is suitable for use in the AM device. The composition is particularly suitable for use in a transmissive AM device. A composition having an optical anisotropy in the range of about 0.08 to 0.25, and also a composition having an optical anisotropy in the range of about 0.10 to 0.30 may be prepared by controlling a proportion of the component compounds or by mixing with any other liquid crystal compound. The composition can be used as the composition having the nematic phase, or as the optically active composition by adding the optically active compound to the composition.

The composition can be used for the AM device. The composition can also be used to a PM device. The composition can also be used for an AM device or a PM device each having a mode such as a PC mode, a TN mode, an STN mode, an ECB mode, an OCB mode, an IPS mode, a VA mode and an FPA mode. Use for an AM device having the TN, OCB, IPS or FFS mode is particularly preferred. In an AM device having the IPS mode or the FFS mode, alignment of liquid crystal molecules in a state in which no voltage is applied may be parallel or perpendicular to a glass substrate. The device may be of a reflective type, a transmissive type or a transflective type. Use for the transmissive device is preferred. The composition can also be used for an amorphous silicon-TFT device or a polycrystal silicon-TFT device. Use for a nematic curvilinear aligned phase (NCAP) device prepared by microencapsulating the composition, or for a polymer dispersed (PD) device in which a three-dimensional network polymer is formed in the composition is allowed.

EXAMPLES

The invention will be described in greater detail by way of Examples. The invention is not limited by the examples. The invention includes a mixture of a composition in Example 1 and a composition in Example 2. The invention also includes a mixture in which at least two of the compositions in Examples were mixed. A prepared compound was identified by a method such as NMR analysis. Characteristics of the compound and the composition were measured by methods described below.

NMR analysis: For measurement, DRX-500 made by Bruker BioSpin Corporation was used. In $^1$H-NMR measurement, a sample was dissolved in a deuterated solvent such as $CDCl_3$, and measurement was carried out under conditions of room temperature, 500 MHz and 16 times of accumulation. Tetramethylsilane was used as an internal standard. In $^{19}$F-NMR measurement, measurement was carried out under conditions of 24 times of accumulation using $CFCl_3$ as an internal standard. In the explanation of nuclear magnetic resonance spectra, s, d, t, q, quin, sex, m stand for a singlet, a doublet, a triplet, a quartet, a quintet, a sextet and a multiplet, respectively, and br being broad.

Gas chromatographic analysis: GC-14B Gas Chromatograph made by Shimadzu Corporation was used for measurement. A carrier gas was helium (2 mL per minute). A sample vaporizing chamber and a detector (FID) were set to 280° C. and 300° C., respectively. A capillary column DB-1 (length 30 m, bore 0.32 mm, film thickness 0.25 μm; dimethylpolysiloxane as a stationary phase, non-polar) made by Agilent Technologies, Inc. was used for separation of component compounds. After the column was kept at 200° C. for 2 minutes, the column was heated to 280° C. at a rate of 5° C. per minute. A sample was prepared in an acetone solution (0.1% by weight), and then 1 microliter of the solution was injected into the sample vaporizing chamber. A recorder was C-R5A Chromatopac made by Shimadzu Corporation or the equivalent thereof. The resulting gas chromatogram showed a retention time of a peak and a peak area corresponding to each of the component compounds.

As a solvent for diluting the sample, chloroform, hexane or the like may also be used. The following capillary columns may also be used for separating component compounds: HP-1 (length 30 m, bore 0.32 mm, film thickness 0.25 μm) made by Agilent Technologies, Inc., Rtx-1 (length 30 m, bore 0.32 mm, film thickness 0.25 μm) made by Restek Corporation and BP-1 (length 30 m, bore 0.32 mm, film thickness 0.25 μm) made by SGE International Pty. Ltd. A capillary column CBP1-M50-025 (length 50 m, bore 0.25 mm, film thickness 0.25 μm) made by Shimadzu Corporation may also be used for the purpose of avoiding an overlap of peaks of the compounds.

A proportion of liquid crystal compounds contained in the composition may be calculated by the method as described below. The mixture of liquid crystal compounds is detected by gas chromatograph (FID). An area ratio of each peak in the gas chromatogram corresponds to the ratio (weight ratio) of the liquid crystal compound. When the capillary columns described above were used, a correction coefficient of each of the liquid crystal compounds may be regarded as 1 (one). Accordingly, the proportion (% by weight) of the liquid crystal compound is calculated from the area ratio of each peak.

Sample for measurement: When characteristics of a composition were measured, the composition was used as was. Upon measuring characteristics of a compound, a sample for measurement was prepared by mixing the compound (15% by weight) with a base liquid crystal (85% by weight). Values of characteristics of the compound were calculated using values obtained by measurement, according to an extrapolation method: (extrapolated value)={(measured value of a sample for measurement)−0.85×(measured value of a base liquid crystal)}/0.15. When a smectic phase (or crystals) precipitated at the ratio thereof at 25° C., a ratio of the compound to the base liquid crystal was changed step by step in the order of (10% by weight:90% by weight), (5% by weight:95% by weight) and (1% by weight:99% by weight). Values of maximum temperature, optical anisotropy, viscosity and dielectric anisotropy with regard to the compound were determined according to the extrapolation method.

The base liquid crystal described below was used. A proportion of the component compounds was expressed in terms of weight percent (% by weight).

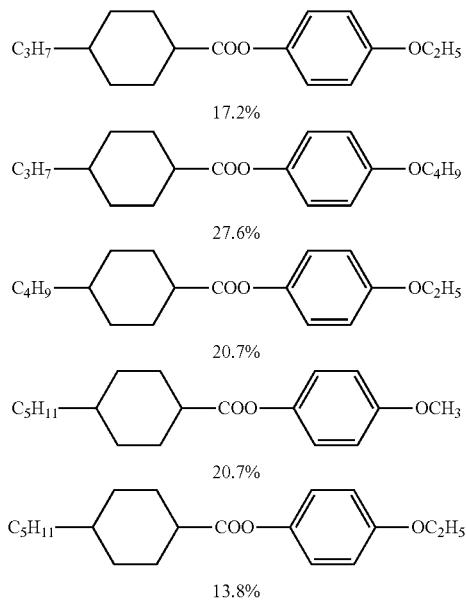

Measuring method: Measurement of characteristics was carried out by the methods described below. Most of the measuring methods are applied as described in the Standard of the Japan Electronics and Information Technology Industries Association (hereinafter, abbreviated as JEITA) (JEITA EIAJ ED-2521B) discussed and established by JEITA, or modified thereon. No thin film transistor (TFT) was attached to a TN device used for measurement.

(1) Maximum temperature of nematic phase (NI; ° C.): A sample was placed on a hot plate in a melting point apparatus equipped with a polarizing microscope and was heated at a rate of 1° C. per minute. Temperature when part of the sample began to change from a nematic phase to an isotropic liquid was measured. A maximum temperature of the nematic phase may be occasionally abbreviated as "maximum temperature."

(2) Minimum temperature of nematic phase (Tc; ° C.): Samples each having a nematic phase were put in glass vials and kept in freezers at temperatures of 0° C., −10° C., −20° C., −30° C. and −40° C. for 10 days, and then liquid crystal phases were observed. For example, when the sample maintained the nematic phase at −20° C. and changed to crystals or a smectic phase at −30° C., Tc of the sample was expressed as Tc<−20° C. A minimum temperature of the nematic phase may be occasionally abbreviated as "minimum temperature."

(3) Viscosity (bulk viscosity; q; measured at 20° C.; mPa·s): A cone-plate (E type) rotational viscometer made by Tokyo Keiki, Inc. was used for measurement.

(4) Viscosity (rotational viscosity; γ1; measured at 25° C.; mPa·s): Measurement was carried out according to the method described in M. Imai et al., Molecular Crystals and Liquid Crystals, Vol. 259, p. 37 (1995). A sample was put in a VA device in which a distance (cell gap) between two glass substrates was 20 micrometers. Voltage was applied stepwise to the device in the range of 39 V to 50 V at an increment of 1 V. After a period of 0.2 second with no voltage application, voltage was applied repeatedly under the conditions of only one rectangular wave (rectangular pulse; 0.2 second) and no voltage application (2 seconds). A peak current and a peak time of a transient current generated by the applied voltage were measured. A value of rotational viscosity was obtained from the measured values and calculation equation (8) on page 40 of the paper presented by M. Imai et al. The dielectric anisotropy required for the calculation was measured according to section (6) described below.

(5) Optical anisotropy (refractive index anisotropy; Δn; measured at 25° C.): Measurement was carried out by an Abbe refractometer with a polarizing plate mounted on an ocular, using light at a wavelength of 589 nanometers. A surface of a main prism was rubbed in one direction, and then a sample was added dropwise onto the main prism. A refractive index n∥ was measured when the direction of polarized light was parallel to the direction of rubbing. A refractive index n⊥ was measured when the direction of polarized light was perpendicular to the direction of rubbing. A value of optical anisotropy was calculated from an equation: Δn=n∥−n⊥.

(6) Dielectric anisotropy (Δ∈; measured at 25° C.): A value of dielectric anisotropy was calculated from an equation: Δ∈=∈∥−∈⊥. A dielectric constant (∈∥ and ∈⊥) was measured as described below.

(1) Measurement of dielectric constant (∈∥): An ethanol (20 mL) solution of octadecyl triethoxysilane (0.16 mL) was applied to a well-cleaned glass substrate. After rotating the glass substrate with a spinner, the glass substrate was heated at 150° C. for 1 hour. A sample was put in a VA device in which a distance (cell gap) between two glass substrates was 4 micrometers, and the device was sealed with an ultraviolet-curable adhesive. Sine waves (0.5 V, 1 kHz) were applied to the device, and after 2 seconds, a dielectric constant (∈∥) in the major axis direction of liquid crystal molecules was measured.

(2) Measurement of dielectric constant (∈⊥): A polyimide solution was applied to a well-cleaned glass substrate. After calcining the glass substrate, rubbing treatment was applied to the alignment film obtained. A sample was put in a TN device in which a distance (cell gap) between two glass substrates was 9 micrometers and a twist angle was 80 degrees. Sine waves (0.5 V, 1 kHz) were applied to the device, and after 2 seconds, a dielectric constant (∈⊥) in the minor axis direction of the liquid crystal molecules was measured.

(7) Threshold voltage (Vth; measured at 25° C.; V): An LCD-5100 luminance meter made by Otsuka Electronics Co., Ltd. was used for measurement. A light source was a halogen lamp. A sample was put in a normally black mode VA device in which a distance (cell gap) between two glass substrates was 4 micrometers and a rubbing direction was anti-parallel, and the device was sealed with an ultraviolet-curable adhesive. A voltage (60 Hz, rectangular waves) to be applied to the device was stepwise increased from 0 V to 20 V at an increment of 0.02 V. On the occasion, the device was irradiated with light from a direction perpendicular to the device, and an amount of light transmitted through the device was measured. A voltage-transmittance curve was prepared, in which the maximum amount of light corresponds to 100% transmittance and the minimum amount of light corresponds to 0% transmittance. A threshold voltage is expressed in terms of a voltage at 10% transmittance.

(8) Voltage holding ratio (VHR-1; measured at 25° C.; %): A TN device used for measurement had a polyimide alignment film, and a distance (cell gap) between two glass substrates was 5 micrometers. A sample was put in the device, and the device was sealed with an ultraviolet-curable adhesive. A pulse voltage (60 microseconds at 5 V) was applied to the TN device and the device was charged. A decaying voltage was measured for 16.7 milliseconds with a high-speed voltmeter, and area A between a voltage curve and a horizontal axis in a unit cycle was obtained. Area B is an area without decay. A voltage holding ratio is expressed in terms of a percentage of area A to area B.

(9) Voltage holding ratio (VHR-2; measured at 80° C.; %): A voltage holding ratio was measured in a manner similar to the procedure described above except that measurement was carried out at 80° C. in place of 20° C. The obtained value was expressed in terms of VHR-2.

(10) Voltage holding ratio (VHR-3; measured at 25 C; %): After a device was irradiated with ultraviolet light, a voltage holding ratio was measured and stability to ultraviolet light was evaluated. A TN device used for measurement had a polyimide alignment film, and a cell gap between two glass substrates was 5 micrometers. A sample was put in the device, and then irradiated with light for 20 minutes. A light source was an ultra high-pressure mercury lamp USH-500D (made by Ushio, Inc.), and a distance between the device and the light source was 20 centimeters. In measurement of VHR-3, a decaying voltage was measured for 16.7 milliseconds. A composition having large VHR-3 has a large stability to ultraviolet light. A value of VHR-3 is preferably 90% or more, and further preferably 95% or more.

(11) Voltage holding ratio (VHR-4; measured at 25 C; %): After a TN device into which a sample was charged was heated in a constant-temperature bath at 80° C. for 500 hours, a voltage holding ratio was measured and stability to heat was evaluated. In measurement of VHR-4, a decaying voltage was measured for 16.7 milliseconds. A composition having large VHR-4 has a large stability to heat.

(12) Response time (τ; measured at 25° C.; ms): An LCD-5100 luminance meter made by Otsuka Electronics Co., Ltd. was used for measurement. A light source was a halogen lamp. A low-pass filter was set at 5 kHz. A sample was put in a normally black mode VA device in which a distance (cell gap) between two glass substrates was 4 micrometers and a rubbing direction was anti-parallel. The device was sealed with an ultraviolet-curable adhesive. A voltage (60 Hz, rectangular waves) was applied to the device. On the occasion, the device was irradiated with light from a direction perpendicular to the device, and an amount of light transmitted through the device was measured. A maximum amount of light corresponds to 100% transmittance and a minimum amount of light corresponds to 0% transmittance. A response time is a period of time required for a change from 90% transmittance to 10% transmittance (fall time; millisecond).

(13) Specific resistance (ρ; measured at 25° C.; Ωcm): In a vessel equipped with electrodes, 1.0 mL of sample was put. A direct current voltage (10 V) was applied to the vessel, and a direct current after 10 seconds was measured. Specific resistance was calculated from the following equation: (Specific resistance)={(voltage)×(electric capacity of a vessel)}/{(direct current)×(dielectric constant of vacuum)}.

The compounds described in Examples were described using symbols according to definitions in Table 3 below. In Table 3, a configuration of 1, 4-cyclohexylene is trans. A parenthesized number next to a symbolized compound in Examples corresponds to the number of the compound. A symbol (–) means any other liquid crystal compound. A proportion (percentage) of the liquid crystal compound is expressed in terms of weight percent (% by weight) based on the weight of the liquid crystal composition. Values of characteristics of the composition were summarized in a last part.

TABLE 3

Method for Description of Compounds using Symbols
R—(A$_1$)—Z$_1$— . . . —Z$_n$—(A$_n$)—R'

| 1) Left-terminal Group R— | Symbol |
|---|---|
| FC$_n$H$_{2n}$— | Fn— |
| C$_n$H$_{2n+1}$— | n- |
| C$_n$H$_{2n+1}$O— | nO— |
| C$_m$H$_{2m+1}$OC$_n$H$_{2n}$— | mOn— |
| CH$_2$=CH— | V— |
| C$_n$H$_{2n+1}$—CH=CH— | nV— |
| CH$_2$=CH—C$_n$H$_{2n}$— | Vn— |
| C$_m$H$_{2m+1}$—CH=CH—C$_n$H$_{2n}$— | mVn— |
| CF$_2$=CH— | VFF— |
| CF$_2$=CH—C$_n$H$_{2n}$— | VFFn— |
| CH$_2$=CH—COO— | AC— |
| CH$_2$=C(CH$_3$)—COO— | MAC— |

| 2) Right-terminal Group —R' | Symbol |
|---|---|
| —C$_n$H$_{2n+1}$ | -n |
| —OC$_n$H$_{2n+1}$ | —On |
| —CH=CH$_2$ | —V |
| —CH=CH—C$_n$H$_{2n+1}$ | —Vn |
| —C$_n$H$_{2n}$—CH=CH$_2$ | —nV |
| —C$_m$H$_{2m}$—CH=CH—C$_n$H$_{2n+1}$ | —mVn |
| —CH=CF$_2$ | —VFF |
| —OCO—CH=CH$_2$ | —AC |
| —OCO—C(CH$_3$)=CH$_2$ | —MAC |

| 3) Bonding Group —Zn— | Symbol |
|---|---|
| —C$_n$H$_{2n}$— | n |
| —COO— | E |
| —CH=CH— | V |
| —CH=CHO— | VO |
| —OCH=CH— | OV |
| —CH$_2$O— | 1O |
| —OCH$_2$— | O1 |

| 4) Ring Structure —An— | Symbol |
|---|---|
| ⬡ | H |

TABLE 3-continued

| | |
|---|---|
| 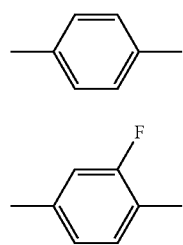 | B |
| 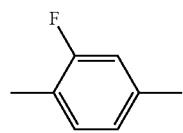 | B(F) |
| 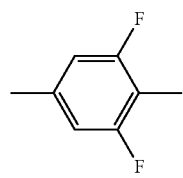 | B(2F) |
| 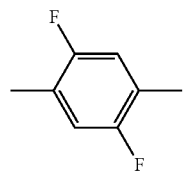 | B(F,F) |
| 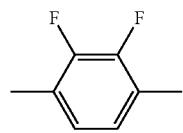 | B(2F,5F) |
| 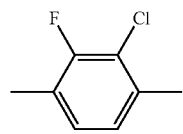 | B(2F,3F) |
| 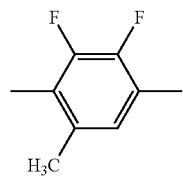 | B(2F,3CL) |
| 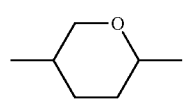 | B(2F,3F,6Me) |
| 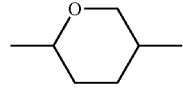 | dh |
| 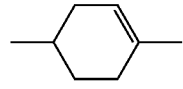 | Dh |
| 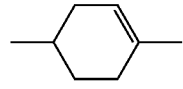 | ch |

TABLE 3-continued

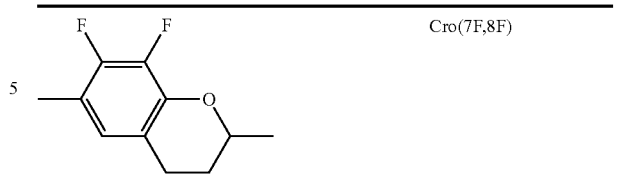

Cro(7F,8F)

5) Examples of Description

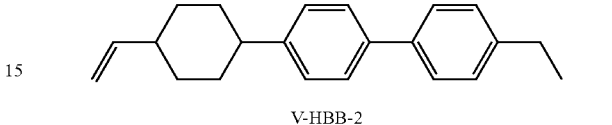

V-HBB-2

Example 1

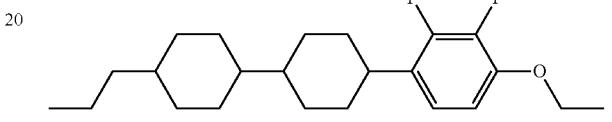

3-HHB(2F,3F)-O2

Example 2

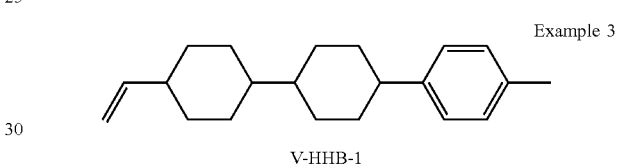

V-HHB-1

Example 3

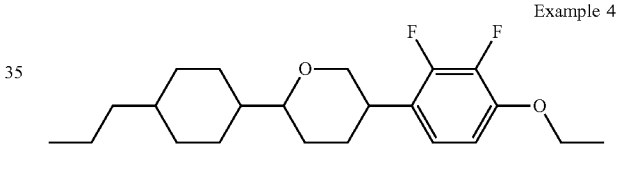

3-HDhB(2F,3F)-O2

Example 4

Comparative Example 1

Example 6 was selected from compositions disclosed in WO 2012-053323A. The reason is that the composition contains a compound similar to compound (1). Components and characteristics of the composition are as described below.

| | | |
|---|---|---|
| 3-HBB-2 | Similar to (1) | 5% |
| 5-BB(2F,3F)-O2 | (2-2) | 5% |
| V2-BB(2F,3F)-O2 | (2-2) | 5% |
| 1V2-BB(2F,3F)-O2 | (2-2) | 3% |
| 2-BB(2F,3F)B-4 | (2-5) | 3% |
| 5-HBB(2F,3F)-O2 | (2-8) | 5% |
| 3-HHB(2F,3CL)-O2 | (2-10) | 3% |
| 5-DhBB(2F,3F)-O2 | (2) | 3% |
| 5-DhB(2F,3F)-O2 | (2) | 3% |
| 3-HH-V | (3-1) | 6% |
| 3-HH-V1 | (3-1) | 5% |
| 3-HH-VFF | (3-1) | 5% |
| 1-BB-1 | (3-3) | 5% |
| 1-BB-5 | (3-3) | 5% |
| 2-BB-3 | (3-3) | 5% |
| 3-BB-5 | (3-3) | 5% |
| 3-HHB-O1 | (3-5) | 3% |
| 5-B(F)BB-3 | (3-6) | 3% |
| 5-HBB(F)B-3 | (3-12) | 3% |
| 5-HH2B(2F,3F)-O2 | (4-3) | 5% |

-continued

| | | |
|---|---|---|
| 3-HH1OB(2F,3F)-O2 | (4-4) | 7% |
| 5-HH1OB(2F,3F)-O2 | (4-4) | 8% |

NI=83.9° C.; Tc≤−20° C.; Δn=0.135; η=18.7 mPa·s; Δ∈=−3.5; VHR-1=99.1%; VHR-2=98.1%; VHR-3=98.2%.

Example 1

| | | |
|---|---|---|
| V-HBB-2 | (1) | 5% |
| V-HBB-4 | (1) | 3% |
| 3-BB(2F,3F)-O4 | (2-2) | 3% |
| V2-BB(2F,3F)-O2 | (2-2) | 11% |
| 1V2-BB(2F,3F)-O2 | (2-2) | 6% |
| 2O-B(2F,3F)B(2F,3F)-O6 | (2-3) | 3% |
| V-HHB(2F,3F)-O1 | (2-4) | 4% |
| V-HHB(2F,3F)-O2 | (2-4) | 11% |
| 2-BB(2F,3F)B-3 | (2-5) | 6% |
| 3-HH-V | (3-1) | 29% |
| 3-HH-V1 | (3-1) | 9% |
| 3-HH1OB(2F,3F)-O2 | (4-4) | 10% |

NI=75.6° C.; Tc<−20° C.; Δn=0.114; Δ∈=−3.1; Vth=2.36 V; η=16.7 mPa·s; VHR-1=99.1%; VHR-2=98.2%.

Example 2

| | | |
|---|---|---|
| V-HBB-2 | (1) | 10% |
| 3-HB(2F,3F)-O4 | (2-1) | 5% |
| 3-BB(2F,3F)-O2 | (2-2) | 10% |
| 2O-BB(2F,3F)-O2 | (2-2) | 3% |
| 3-dhBB(2F,3F)-O2 | (2-9) | 3% |
| 2-HH-3 | (3-1) | 23% |
| 3-HH-O1 | (3-1) | 6% |
| 4-HH-V1 | (3-1) | 9% |
| 1-BB-3 | (3-3) | 3% |
| 2-HH1OB(2F,3F)-O2 | (4-4) | 7% |
| 3-HH1OB(2F,3F)-O2 | (4-4) | 21% |

NI=72.6° C.; Tc<−20° C.; Δn=0.095; Δ∈=−3.3; Vth=2.17 V; η=16.4 mPa·s.

Example 3

| | | |
|---|---|---|
| V-HBB-2 | (1) | 8% |
| 3-BB(2F,3F)-O2 | (2-2) | 10% |
| 5-BB(2F,3F)-O2 | (2-2) | 4% |
| V2-BB(2F,3F)-O2 | (2-2) | 8% |
| V-HHB(2F,3F)-O1 | (2-4) | 6% |
| V-HHB(2F,3F)-O2 | (2-4) | 12% |
| V2-HHB(2F,3F)-O2 | (2-4) | 8% |
| 3-HDhB(2F,3F)-O2 | (2-7) | 7% |
| 2-HH-3 | (3-1) | 14% |
| 3-HH-V1 | (3-1) | 9% |
| 3-HB-O2 | (3-2) | 8% |
| V-HHB-1 | (3-5) | 3% |
| 3-HHEBH-3 | (3-8) | 3% |

NI=83.2° C.; Tc<−20° C.; Δn=0.109; Δ∈=−3.3; Vth=2.22 V; η=13.2 mPa·s.

Example 4

| | | |
|---|---|---|
| V-HBB-1 | (1) | 6% |
| V2-HBB-1 | (1) | 3% |
| V2-HBB(2F,3F)-O2 | (2-8) | 5% |
| 3-HHB(2F,3CL)-O2 | (2-10) | 4% |
| 3-HBB(2F,3CL)-O2 | (2-11) | 6% |
| 5-HBB(2F,3CL)-O2 | (2-11) | 6% |
| 3-HH-V | (3-1) | 24% |
| V-HHB-1 | (3-5) | 5% |
| 2-BB(F)B-3 | (3-7) | 3% |
| 3-H2B(2F,3F)-O2 | (4-1) | 18% |
| 5-H2B(2F,3F)-O2 | (4-1) | 17% |
| 3-HH2B(2F,3F)-O2 | (4-3) | 3% |

NI=73.8° C.; Tc<−20° C.; Δn=0.103; Δ∈=−2.8; Vth=2.31 V; η=15.9 mPa·s.

Example 5

| | | |
|---|---|---|
| V-HBB-2 | (1) | 11% |
| V2-HBB-3 | (1) | 3% |
| 1V2-BB(2F,3F)-O4 | (2-2) | 4% |
| 3-HHB(2F,3F)-O2 | (2-4) | 7% |
| V-HHB(2F,3F)-O1 | (2-4) | 5% |
| V-HHB(2F,3F)-O2 | (2-4) | 8% |
| 2-HBB(2F,3F)-O2 | (2-8) | 4% |
| 5-HBB(2F,3F)-O2 | (2-8) | 7% |
| V-HBB(2F,3F)-O2 | (2-8) | 3% |
| 2-HH-3 | (3-1) | 21% |
| 2-HH-5 | (3-1) | 3% |
| 3-HB-O2 | (3-2) | 4% |
| 1-BB-3 | (3-3) | 6% |
| 2-H1OB(2F,3F)-O2 | (4-2) | 3% |
| 3-H1OB(2F,3F)-O2 | (4-2) | 11% |

NI=77.0° C.; Tc<−20° C.; Δn=0.108; Δ∈=−2.8; Vth=2.21 V; η=16.7 mPa·s.

Example 6

| | | |
|---|---|---|
| V-HBB-3 | (1) | 5% |
| 3-HB(2F,3F)-O2 | (2-1) | 7% |
| V-HB(2F,3F)-O2 | (2-1) | 12% |
| V-HB(2F,3F)-O4 | (2-1) | 4% |
| 3-HBB(2F,3F)-O2 | (2-8) | 10% |
| 5-HBB(2F,3F)-O2 | (2-8) | 7% |
| 1V2-HBB(2F,3F)-O2 | (2-8) | 3% |
| 3-HHB(2F,3CL)-O2 | (2-10) | 5% |
| 2-HH-3 | (3-1) | 22% |
| 3-HH-4 | (3-1) | 4% |
| 4-HH-V1 | (3-1) | 3% |
| 3-HB-O2 | (3-2) | 6% |
| 5-HB-O2 | (3-2) | 5% |
| 3-HHB-1 | (3-5) | 4% |
| 5-HBB(F)B-2 | (3-12) | 3% |

NI=71.5° C.; Tc<−20° C.; Δn=0.098; Δ∈=−2.4; Vth=2.36 V; η=15.1 mPa·s.

Example 7

| | | |
|---|---|---|
| V-HBB-2 | (1) | 6% |
| 1V2-BB(2F,3F)-O2 | (2-2) | 10% |
| V-HHB(2F,3F)-O1 | (2-4) | 8% |
| V-HHB(2F,3F)-O2 | (2-4) | 7% |
| 3-HH-V | (3-1) | 27% |
| 5-HH-V | (3-1) | 3% |
| 3-HH-V1 | (3-1) | 8% |

-continued

| | | |
|---|---|---|
| 3-HH-VFF | (3-1) | 4% |
| V2-HHB-1 | (3-5) | 4% |
| 5-B(F)BB-2 | (3-6) | 3% |
| 3-H1OB(2F,3F)-O2 | (4-2) | 12% |
| 3-HH1OB(2F,3F)-O2 | (4-4) | 5% |
| 3-H1OCro(7F,8F)-5 | (4-7) | 3% |

NI=72.9° C.; Tc<−20° C.; Δn=0.097; Δ∈=−3.2; Vth=2.16 V; η=16.9 mPa·s.

Example 8

| | | |
|---|---|---|
| V-HBB-2 | (1) | 3% |
| V2-HBB-2 | (1) | 3% |
| 3-BB(2F,3F)-O2 | (2-2) | 8% |
| 2O-BB(2F,3F)-O2 | (2-2) | 3% |
| 3-HDhB(2F,3F)-O2 | (2-7) | 5% |
| 3-HH-V | (3-1) | 31% |
| 3-HH-V1 | (3-1) | 4% |
| V2-BB-1 | (3-3) | 6% |
| V2-HHB-1 | (3-5) | 8% |
| 5-HBBH-3 | (3-10) | 3% |
| 3-H1OB(2F,3F)-O2 | (4-2) | 13% |
| 3-HH1OB(2F,3F)-O2 | (4-4) | 7% |
| 3-HEB(2F,3F)B(2F,3F)-O2 | (4-6) | 3% |
| 3-HH1OCro(7F,8F)-5 | (4-8) | 3% |

NI=74.4° C.; Tc<−20° C.; Δn=0.100; Δ∈=−3.4; Vth=2.22 V; η=16.6 mPa·s.

Example 9

| | | |
|---|---|---|
| V-HBB-2 | (1) | 5% |
| 3-HB(2F,3F)-O2 | (2-1) | 8% |
| 3-HB(2F,3F)-O4 | (2-1) | 9% |
| 5-HB(2F,3F)-O4 | (2-1) | 5% |
| V2-BB(2F,3F)-O2 | (2-2) | 6% |
| 3-DhHB(2F,3F)-O2 | (2-6) | 3% |
| 3-HBB(2F,3F)-O2 | (2-8) | 9% |
| 5-HBB(2F,3F)-O2 | (2-8) | 8% |
| 2-HH-3 | (3-1) | 22% |
| 3-HH-4 | (3-1) | 7% |
| F3-HH-V | (3-1) | 3% |
| 7-HB-1 | (3-2) | 4% |
| 3-HHB-3 | (3-5) | 3% |
| 5-HB(F)BH-3 | (3-11) | 5% |
| 1O1-HBBH-5 | (—) | 3% |

NI=73.6° C.; Tc<−20° C.; Δn=0.094; Δ∈=−2.3; Vth=2.40 V; η=16.0 mPa·s.

Example 10

| | | |
|---|---|---|
| V-HBB-2 | (1) | 7% |
| 3-BB(2F,3F)-O2 | (2-2) | 10% |
| 5-BB(2F,3F)-O2 | (2-2) | 6% |
| V2-BB(2F,3F)-O2 | (2-2) | 5% |
| V-HHB(2F,3F)-O1 | (2-4) | 6% |
| V-HHB(2F,3F)-O2 | (2-4) | 12% |
| V2-HHB(2F,3F)-O2 | (2-4) | 5% |
| 2-HH-3 | (3-1) | 14% |
| 3-HH-V1 | (3-1) | 7% |
| 3-HB-O2 | (3-2) | 4% |
| 3-HHEH-3 | (3-4) | 3% |
| V-HHB-1 | (3-5) | 11% |
| 3-HB(F)HH-2 | (3-9) | 3% |

| | | |
|---|---|---|
| 2-H1OB(2F,3F)-O2 | (4-2) | 4% |
| 3-DhH1OB(2F,3F)-O2 | (4-5) | 3% |

NI=82.1° C.; Tc<−20° C.; Δn=0.106; Δ∈=−2.9; Vth=2.36 V; η=13.9 mPa·s.

The compositions in Examples 1 to 10 have a smaller viscosity in comparison with the composition in Comparative Example 1. Accordingly, the liquid crystal composition of the invention is concluded to have further excellent characteristics.

INDUSTRIAL APPLICABILITY

A liquid crystal composition of the invention satisfies at least one of characteristics such as a high maximum temperature of a nematic phase, a low minimum temperature of the nematic phase, a small viscosity, a suitable optical anisotropy, a large negative dielectric anisotropy, a large specific resistance, a high stability to ultraviolet light or heat, or a suitable balance regarding at least two of the characteristics. A liquid crystal display device including the composition has characteristics such as a short response time, a large voltage holding ratio, a low threshold voltage, a large contrast ratio, a long service life, and thus can be used for a liquid crystal projector, a liquid crystal television and so forth.

What is claimed is:

1. A liquid crystal composition that has a negative dielectric anisotropy, and consists essentially of at least one compound selected from compounds represented by formula (1) as a first component, at least one compound selected from compounds represented by formula (2) as a second component, at least one compound selected from compounds represented by formula (3) as a third component, and at least one compound selected from compounds represented by formula (4) as a fourth component, and optionally contains at least one polymerizable compound selected from compounds represented by formula (5) as an additive component:

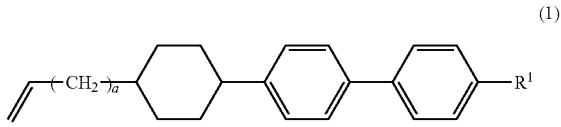

(1)

wherein, in formula (1), $R^1$ is alkyl having 1 to 12 carbons, alkoxy having 1 to 12 carbons, alkenyl having 2 to 12 carbons, or alkenyl having 2 to 12 carbons in which at least one piece of hydrogen is replaced by fluorine; and a is an integer from 0 to 12;

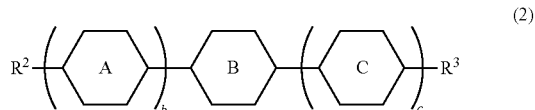

(2)

in formula (2), $R^2$ and $R^3$ are independently alkyl having 1 to 12 carbons, alkoxy having 1 to 12 carbons, alkenyl having 2 to 12 carbons, alkenyloxy having 2 to 12 carbons, alkyl having 1 to 12 carbons in which at least one piece of hydrogen is replaced by fluorine, or alkenyl having 2 to 12 carbons in which at least one piece of hydrogen is replaced by fluorine; ring A and ring C are independently 1,4-cyclohexylene, 1,4-cyclohexenylene, 1,4-phenylene, or 1,4-phenylene in which at least one piece of hydrogen is replaced by fluorine or chlorine; ring B is 2,3-difluoro-1,4-phenylene, 2-chloro-3-fluoro-1,4-phenylene, 2,3-difluoro-5-methyl-1,4-phenylene, 3,4,5-trifluoronaphthalene-2,6-diyl or 7,8-difluorochroman-2,6-diyl; b is 1, 2 or 3; c is 0 or 1; and a sum of b and c is 3 or less;

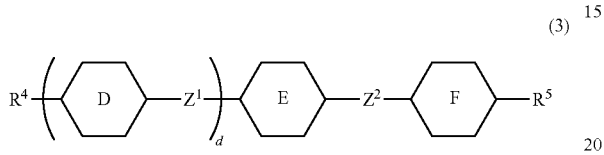
(3)

in formula (3), $R^4$ and $R^5$ are independently alkyl having 1 to 12 carbons, alkoxy having 1 to 12 carbons, alkenyl having 2 to 12 carbons, alkyl having 1 to 12 carbons in which at least one piece of hydrogen is replaced by fluorine, or alkenyl having 2 to 12 carbons in which at least one piece of hydrogen is replaced by fluorine; ring D, ring E and ring F are independently 1,4-cyclohexylene, 1,4-phenylene, 2-fluoro-1,4-phenylene or 2,5-difluoro-1,4-phenylene; $Z^1$ and $Z^2$ are independently a single bond, —$CH_2CH_2$—, —$CH_2O$—, —$OCH_2$—, —COO— or —OCO—; d is 0, 1 or 2; in which ring E is 1,4-cyclohexylene, 2-fluoro-1,4-phenylene or 2,5-difluoro-1,4-phenylene when d is 1;

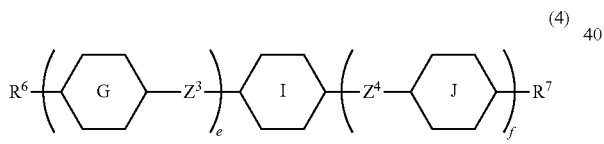
(4)

in formula (4), $R^6$ and $R^7$ are independently alkyl having 1 to 12 carbons, alkoxy having 1 to 12 carbons, alkenyl having 2 to 12 carbons, alkenyloxy having 2 to 12 carbons, alkyl having 1 to 12 carbons in which at least one piece of hydrogen is replaced by fluorine, or alkenyl having 2 to 12 carbons in which at least one piece of hydrogen is replaced by fluorine; ring G and ring J are independently 1,4-cyclohexylene, 1,4-cyclohexenylene, 1,4-phenylene, or 1,4-phenylene in which at least one piece of hydrogen was replaced by fluorine or chlorine; ring I is 2,3-difluoro-1,4-phenylene, 2-chloro-3-fluoro-1,4-phenylene, 2,3-difluoro-5-methyl-1,4-phenylene, 3,4,5-trifluoronaphthalene-2,6-diyl or 7,8-difluorochroman-2,6-diyl; $Z^3$ and $Z^4$ are independently a single bond, —$CH_2CH_2$—, —$CH_2O$—, —$OCH_2$—, —COO— or —OCO—; at least one of $Z^3$ and $Z^4$ is —$CH_2CH_2$—, —$CH_2O$—, —$OCH_2$—, —COO— or —OCO—; e is 1, 2 or 3; f is 0 or 1; and a sum of e and f is 3 or less; and

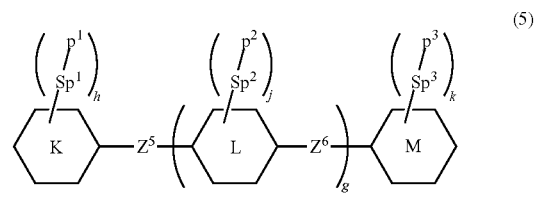
(5)

in formula (5), ring K and ring M are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one piece of hydrogen may be replaced by halogen, alkyl having 1 to 12 carbons, alkoxy having 1 to 12 carbons, or alkyl having 1 to 12 carbons in which at least one piece of hydrogen is replaced by halogen; ring L is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one piece of hydrogen may be replaced by halogen, alkyl having 1 to 12 carbons, alkoxy having 1 to 12 carbons, or alkyl having 1 to 12 carbons in which at least one piece of hydrogen is replaced by halogen; $Z^5$ and $Z^6$ are independently a single bond or alkylene of 1 to 10 carbons, and in the alkylene, at least one piece of —$CH_2$— may be replaced by —O—, —CO—, —COO— or —OCO—, at least one piece of —$CH_2$—$CH_2$— may be replaced by —CH=CH—, —C($CH_3$)=CH—, —CH=C($CH_3$)— or —C($CH_3$)=C($CH_3$)—, and in the groups, at least one piece of hydrogen may be replaced by fluorine or chlorine; $P^1$, $P^2$ and $P^3$ are independently a polymerizable group; $Sp^1$, $Sp^2$ and $Sp^3$ are independently a single bond or alkylene having 1 to 10 carbons, and in the alkylene, at least one piece of —$CH_2$— may be replaced by —O—, —COO—, —OCO— or —OCOO—, at least one piece of —$CH_2$—$CH_2$— may be replaced by —CH=CH— or and in the groups, at least one piece of hydrogen may be replaced by fluorine or chlorine; g is 0, 1 or 2; h, j and k are independently 0, 1, 2, 3 or 4; and a sum of h, j and k is 1 or more.

2. The liquid crystal composition according to claim 1, wherein a proportion of the first component is in the range of 3% by weight to 30% by weight based on the weight of the liquid crystal composition.

3. The liquid crystal composition according to claim 1, containing at least one compound selected from the group of compounds represented by formulas (2-1) to (2-5), (2-8), (2-10) and (2-11) as the second component:

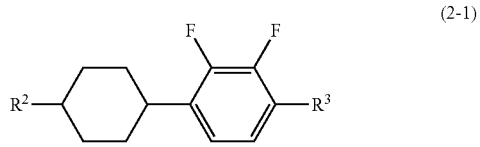
(2-1)

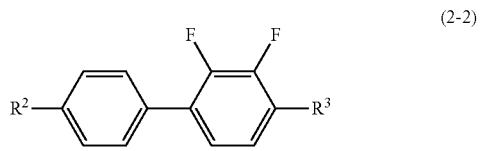
(2-2)

-continued

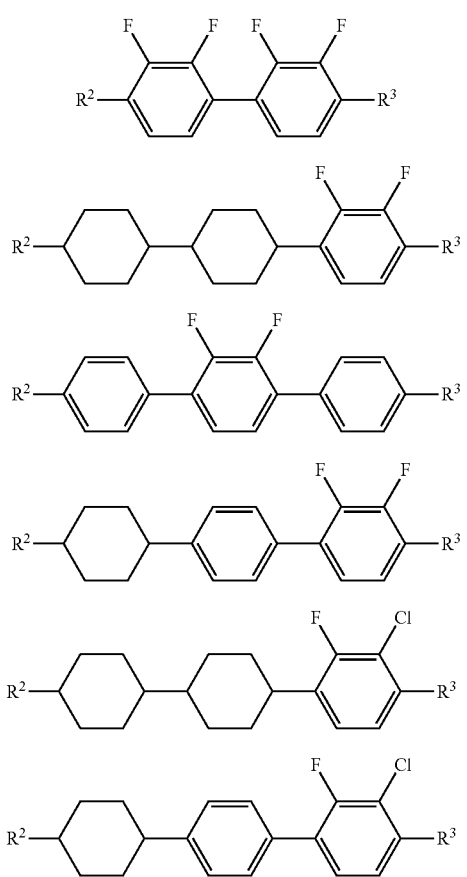

wherein, in formulas (2-1) to (2-5), (2-8), (2-10) and (2-11), $R^2$ and $R^3$ are independently alkyl having 1 to 12 carbons, alkoxy having 1 to 12 carbons, alkenyl having 2 to 12 carbons, alkenyloxy having 2 to 12 carbons, alkyl having 1 to 12 carbons in which at least one piece of hydrogen is replaced by fluorine, or alkenyl having 2 to 12 carbons in which at least one piece of hydrogen is replaced by fluorine.

4. The liquid crystal composition according to claim 1, wherein a proportion of the second component is in the range of 5% by weight to 70% by weight based on the weight of the liquid crystal composition.

5. The liquid crystal composition according to claim 1, containing at least one compound selected from the group of compounds represented by formulas (3-1) to (3-12) as the third component:

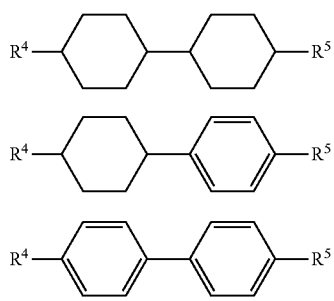

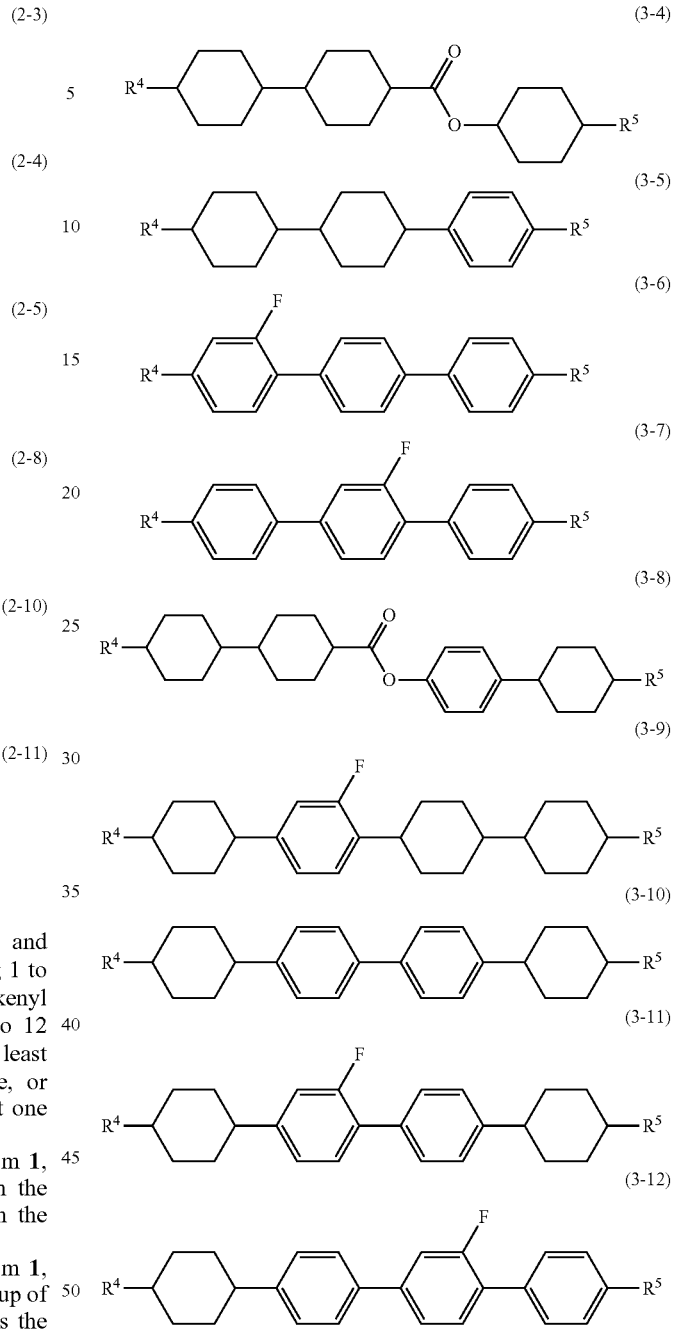

wherein, in formulas (3-1) to (3-12), $R^4$ and $R^5$ are independently alkyl having 1 to 12 carbons, alkoxy having 1 to 12 carbons, alkenyl having 2 to 12 carbons, alkyl having 1 to 12 carbons in which at least one piece of hydrogen is replaced by fluorine, or alkenyl having 2 to 12 carbons in which at least one piece of hydrogen is replaced by fluorine.

6. The liquid crystal composition according to claim 1, wherein a proportion of the third component is in the range of 10% by weight to 90% by weight based on the weight of the liquid crystal composition.

7. The liquid crystal composition according to claim 1, containing at least one compound selected from the group of compounds represented by formulas (4-1) to (4-4) and (4-6) to (4-8) as the fourth component:

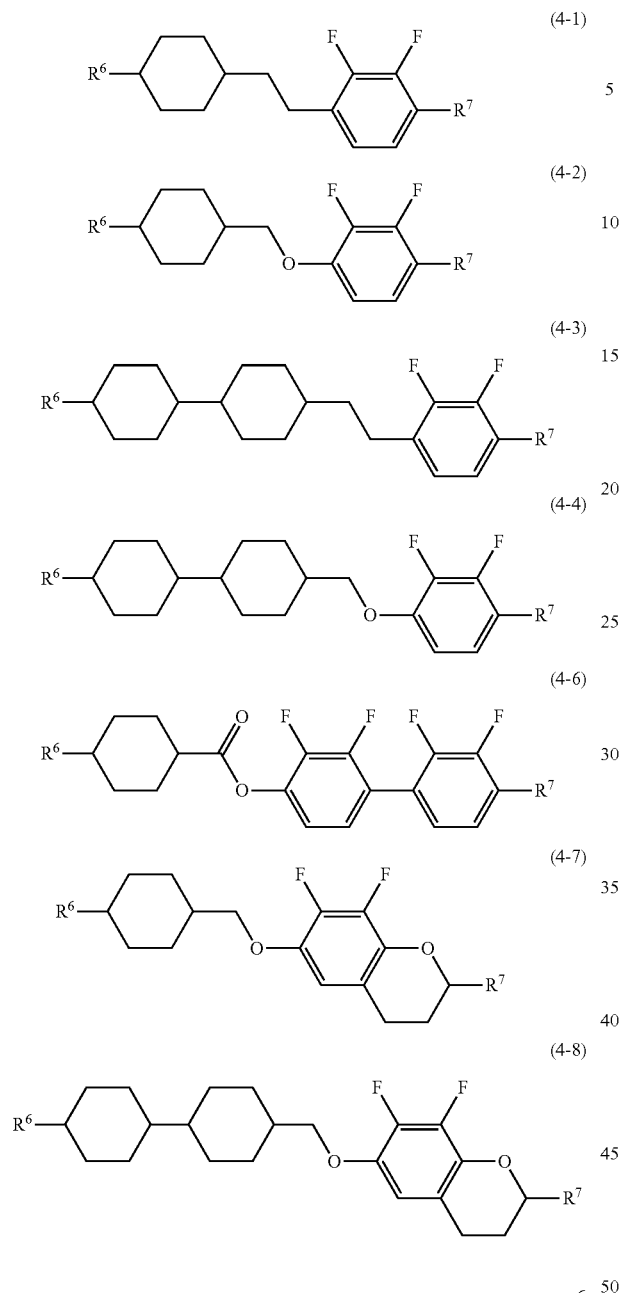

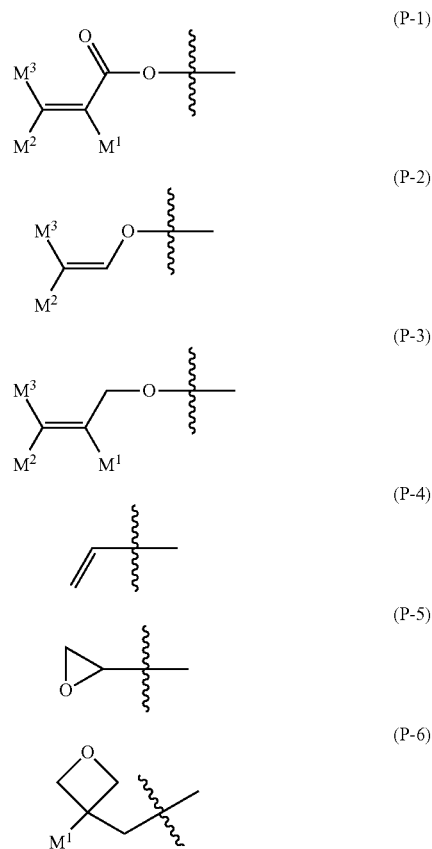

wherein, in formulas (4-1) to (4-4) and (4-6) to (4-8), $R^6$ and $R^7$ are independently alkyl having 1 to 12 carbons, alkoxy having 1 to 12 carbons, alkenyl having 2 to 12 carbons, alkenyloxy having 2 to 12 carbons, alkyl having 1 to 12 carbons in which at least one piece of hydrogen is replaced by fluorine, or alkenyl having 2 to 12 carbons in which at least one piece of hydrogen is replaced by fluorine.

8. The liquid crystal composition according to claim 1, wherein a proportion of the fourth component is in the range of 5% by weight to 60% by weight based on the weight of the liquid crystal composition.

9. The liquid crystal composition according to claim 1, wherein, in formula (5) $P^1$, $P^2$ and $P^3$ are independently a polymerizable group selected from the group of groups represented by formulas (P-1) to (P-6):

wherein, in formulas (P-1) to (P-6), $M^1$, $M^2$ and $M^3$ are independently hydrogen, fluorine, alkyl having 1 to 5 carbons, or alkyl having 1 to 5 carbons in which at least one piece of hydrogen is replaced by halogen; and when both $P^1$ and $P^3$ are a group represented by formula (P-4), in formula (5), at least one of Sp' and $Sp^a$ is alkylene in which at least one piece of —$CH_2$— is replaced by —O—, —COO—, —OCO— or —OCOO—.

10. The liquid crystal composition according to claim 1, containing at least one polymerizable compound selected from the group of compounds represented by formulas (5-1) to (5-27) as the additive component:

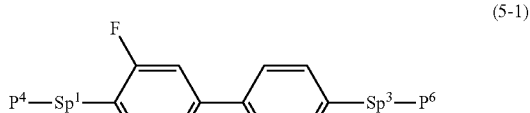

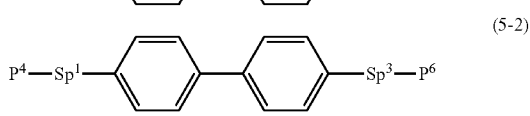

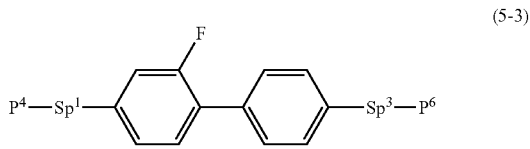

-continued
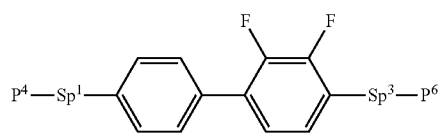 (5-4)
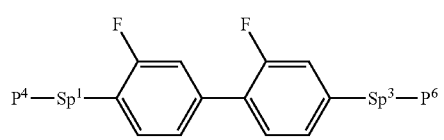 (5-5)
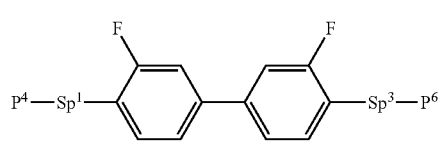 (5-6)
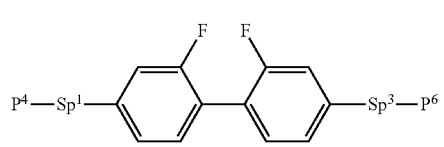 (5-7)
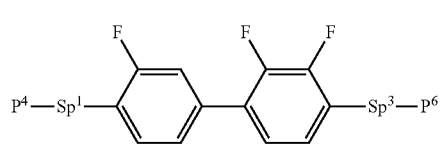 (5-8)
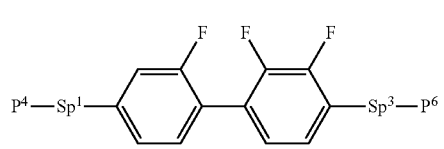 (5-9)
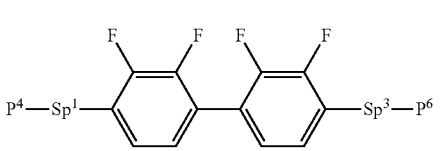 (5-10)
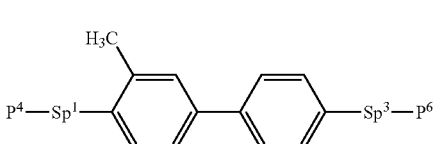 (5-11)
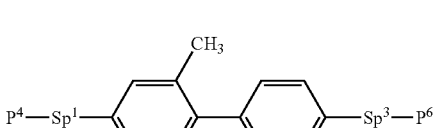 (5-12)
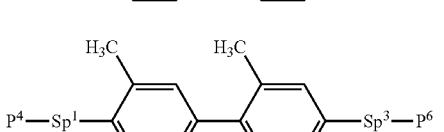 (5-13)
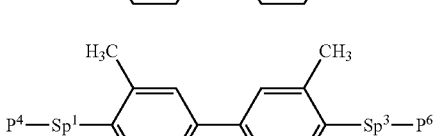 (5-14)
-continued
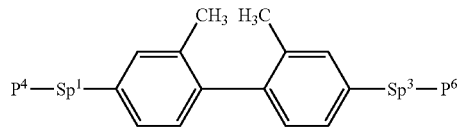 (5-15)
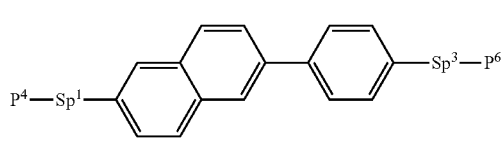 (5-16)
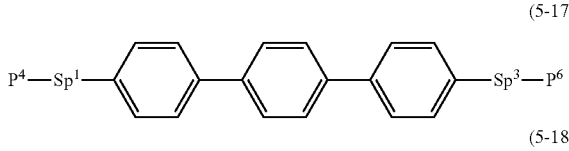 (5-17)
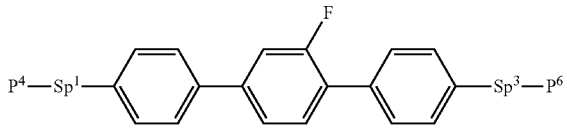 (5-18)
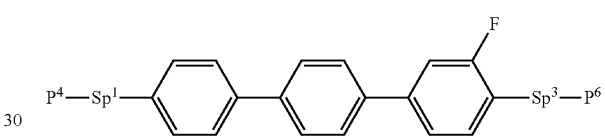 (5-19)
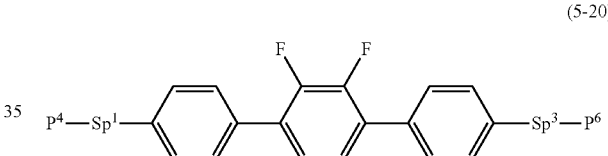 (5-20)
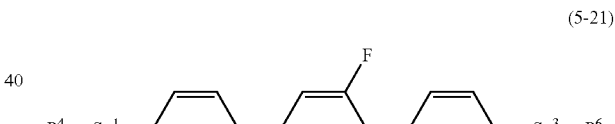 (5-21)
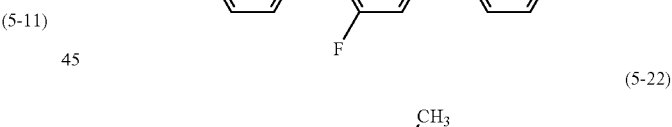 (5-22)
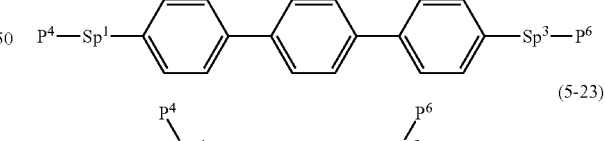 (5-23)
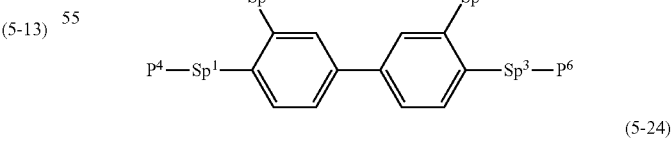 (5-24)

(5-25)
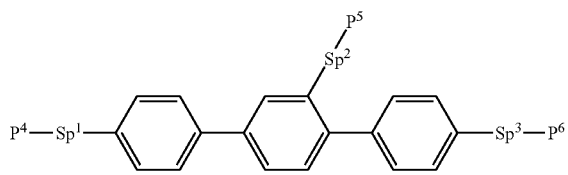

(5-26)
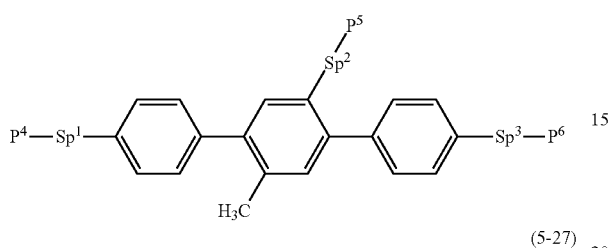

(5-27)
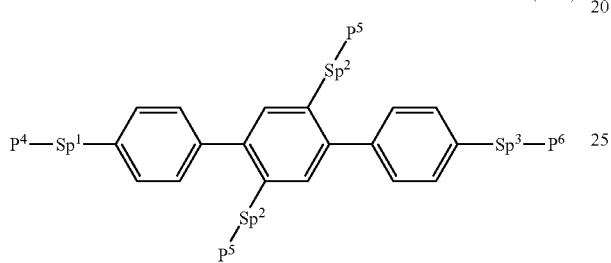

wherein, in formulas (5-1) to (5-27), $P^4$, $P^5$ and $P^6$ are independently a polymerizable group selected from the group of groups represented by formulas (P-1) to (P-3):

(P-1)
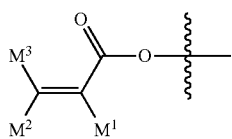

(P-2)
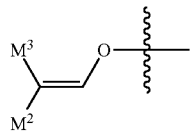

(P-3)
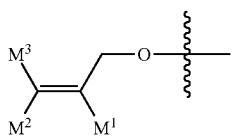

wherein, in formulas (P-1) to (P-3), $M^1$, $M^2$ and $M^3$ are independently hydrogen, fluorine, alkyl having 1 to 5 carbons, or alkyl having 1 to 5 carbons in which at least one piece of hydrogen is replaced by halogen; and in formulas (5-1) to (5-27), $Sp^1$, $Sp^2$ and $Sp^a$ are independently a single bond or alkylene having 1 to 10 carbons, and in the alkylene, at least one piece of —$CH_2$— may be replaced by —O—, —COO—, —OCO— or —OCOO—, at least one piece of —$CH_2$—$CH_2$— may be replaced by —CH═CH— or —C≡C— and in the groups, at least one piece of hydrogen may be replaced by fluorine or chlorine.

11. The liquid crystal composition according to claim 1, wherein a proportion of the additive component is in the range of 0.03% by weight to 10% by weight based on the weight of the liquid crystal composition.

12. A liquid crystal display device, including the liquid crystal composition according to claim 1.

13. The liquid crystal display device according to claim 12, wherein an operating mode in the liquid crystal display device is an IPS mode, a VA mode, an FFS mode or an FPA mode, and a driving mode in the liquid crystal display device is an active matrix mode.

14. A polymer sustained alignment mode liquid crystal display device, wherein the liquid crystal display device includes the liquid crystal composition according to claim 1, and a polymerizable compound in the liquid crystal composition is polymerized.

* * * * *